US011141499B2

(12) United States Patent
Corsetti et al.

(10) Patent No.: US 11,141,499 B2
(45) Date of Patent: Oct. 12, 2021

(54) SANITIZATION SYSTEM

(71) Applicants: Christopher Alexander Corsetti, Newmarket (CA); Robert Joseph Leonetti, Newmarket (CA)

(72) Inventors: Christopher Alexander Corsetti, Newmarket (CA); Robert Joseph Leonetti, Newmarket (CA)

( * ) Notice: Subject to any disclaimer, the term of this patent is extended or adjusted under 35 U.S.C. 154(b) by 85 days.

(21) Appl. No.: 16/341,893

(22) PCT Filed: Oct. 19, 2016

(86) PCT No.: PCT/CA2016/051208
§ 371 (c)(1),
(2) Date: Apr. 13, 2019

(87) PCT Pub. No.: WO2018/072000
PCT Pub. Date: Apr. 26, 2018

(65) Prior Publication Data
US 2019/0240362 A1 Aug. 8, 2019

(51) Int. Cl.
*A61L 2/10* (2006.01)
*E05B 1/00* (2006.01)
(Continued)

(52) U.S. Cl.
CPC .................... *A61L 2/10* (2013.01); *A61L 9/20* (2013.01); *E05B 1/0069* (2013.01); *E05B 39/00* (2013.01);
(Continued)

(58) Field of Classification Search
CPC .......... A61L 2/10; A61L 9/20; A61L 2202/11; A61L 2202/14; A61L 2202/25;
(Continued)

(56) References Cited

U.S. PATENT DOCUMENTS 5,871,522 A 2/1999 Sentilles
6,471,738 B1 10/2002 Thompson et al.
(Continued)

FOREIGN PATENT DOCUMENTS

CA 2891152 5/2014
CA 2939722 11/2015
(Continued)

OTHER PUBLICATIONS

"How do Motion Sensors Work? A Beginners Guide by SafeWise", URL: http://www.safewise.com/resources/motion-sensor-guide, 2015.
(Continued)

*Primary Examiner* — Regina M Yoo

(57) ABSTRACT

An apparatus includes a sanitization system configured to sanitize, at least in part, an interior space of a room. The sanitization system includes a control system configured to be positioned relative to the interior space of the room. The control system is also configured to be in electrical communication with: (A) a sensor assembly configured to be positioned in the interior space of the room, (B) a door-locking mechanism configured to be operatively connected to a door, in which the door is an entrance to the interior space of the room, and (C) a sanitation-light source configured to be positionable in the interior space of the room.

19 Claims, 12 Drawing Sheets

(51) Int. Cl.
*A61L 9/20* (2006.01)
*E05B 39/00* (2006.01)
*G05B 19/042* (2006.01)

(52) U.S. Cl.
CPC ........ *A61L 2202/11* (2013.01); *A61L 2202/14* (2013.01); *A61L 2202/25* (2013.01); *A61L 2209/111* (2013.01); *G05B 19/042* (2013.01)

(58) Field of Classification Search
CPC .. A61L 2209/111; E05B 39/00; E05B 1/0069; G05B 19/042
See application file for complete search history.

(56) References Cited

U.S. PATENT DOCUMENTS

| | | | |
|---|---|---|---|
| 7,357,296 B2 * | 4/2008 | Stemmle | A47G 29/12 |
| | | | 232/17 |
| 7,507,369 B2 * | 3/2009 | Lu | A61L 2/04 |
| | | | 219/679 |
| 8,084,756 B2 | 12/2011 | Tokhtuev et al. | |
| 8,473,097 B2 * | 6/2013 | Shoenfeld | A61L 2/10 |
| | | | 700/237 |
| 8,662,705 B2 | 3/2014 | Roberts | |
| 8,865,065 B2 * | 10/2014 | Kain | A61L 2/24 |
| | | | 422/28 |
| 9,208,676 B2 * | 12/2015 | Fadell | H04L 12/2803 |
| 9,327,040 B2 * | 5/2016 | Kain | A61L 2/24 |
| 9,333,274 B2 | 5/2016 | Peterson et al. | |
| 9,336,636 B2 * | 5/2016 | Soana | G07C 9/38 |
| 9,511,163 B2 * | 12/2016 | Larsen | A61L 9/20 |
| 10,065,740 B2 * | 9/2018 | Childress | B08B 5/04 |
| 10,133,262 B2 * | 11/2018 | Stratmann | E05F 15/75 |
| 10,257,474 B2 * | 4/2019 | Nadathur | H04W 76/11 |
| 10,366,205 B2 * | 7/2019 | Waterson | G16H 10/40 |
| 10,370,695 B2 * | 8/2019 | Kanhye | C12Q 1/04 |
| 10,918,748 B2 * | 2/2021 | Childress | A61L 2/10 |
| 2002/0031460 A1 | 3/2002 | Kulp | |
| 2005/0187596 A1 | 8/2005 | Fiset | |
| 2005/0194026 A1 * | 9/2005 | Lu | A61L 2/24 |
| | | | 134/105 |
| 2007/0053188 A1 | 3/2007 | New et al. | |
| 2008/0134420 A1 | 6/2008 | Ho | |
| 2008/0265179 A1 | 10/2008 | Havens et al. | |
| 2012/0153783 A1 * | 6/2012 | Shoenfeld | A61L 2/10 |
| | | | 312/209 |
| 2012/0144569 A1 | 7/2012 | Kodat | |
| 2012/0282135 A1 | 11/2012 | Trapani | |
| 2014/0060104 A1 | 3/2014 | Shur et al. | |
| 2015/0004061 A1 * | 1/2015 | Kain | A61L 2/24 |
| | | | 422/116 |
| 2015/0025300 A1 * | 1/2015 | Hill | A61L 9/16 |
| | | | 600/21 |
| 2015/0347910 A1 * | 12/2015 | Fadell | H04W 4/80 |
| | | | 706/46 |
| 2016/0030610 A1 | 2/2016 | Peterson et al. | |
| 2017/0049915 A1 * | 2/2017 | Brais | A61L 2/10 |

FOREIGN PATENT DOCUMENTS

| | | |
|---|---|---|
| WO | 2010115183 | 10/2010 |
| WO | 2014036080 | 3/2014 |
| WO | 2015168783 | 11/2015 |

OTHER PUBLICATIONS

"UV Sterlization, Ultraviolet Light Sterilization, Medical UV", URL: http://www.americanultraviolet.com/uv-sterilization.cfml, 2016.

* cited by examiner

SANITIZATION SYSTEM

TECHNICAL FIELD

This document relates to the technical field of (and is not limited to) a sanitization system configured to sanitize, at least in part, an interior space of a room (and method therefor).

BACKGROUND

Room maintenance for a room is an important task, especially for rooms, such as restrooms, washrooms, etc., which may be frequently used.

SUMMARY

It will be appreciated that there exists a need to mitigate (at least in part) at least one problem associated with the existing sanitization systems configured for use with rooms (also called the existing technology). After much study of the known systems and methods with experimentation, an understanding of the problem and its solution has been identified and is articulated as follows:

For instance, and not limited thereto, the lack of upkeep of restrooms (or other types of rooms) can affect public perceptions. It is a challenge to uncover what it takes to keep this critical area in top shape. For instance, when it comes to public restrooms, there are two important jobs: cleaning for appearance (aesthetics) and cleaning for health (disinfecting). Maintaining a visibly clean restroom is important for influencing user perception (clean appearance), but harmful microorganisms (which are associated with outbreaks of illness such as *Shigella, Salmonella*, Hepatitis A, *E. coli*, and/or norovirus) are routinely found in restrooms. Keeping a restroom disinfected may help prevent the spread of illness-causing germs to building occupants and the community at large, especially during the winter months.

Room cleaning, such as restroom cleaning, has an impact on overall public health by helping to prevent the spread of disease. However, many people are not aware of all the risks associated with the spread of germs in the restroom. Many people have an impression that public restrooms harbor germs. Restroom handles (restroom door handles, faucet handles, and toilet or urinal handles) may harbor the most illness-causing germs and bacteria. The feminine hygiene trash can has one of the highest concentrations of germs.

Keeping on top of restroom cleaning can be demanding for people. What is needed is a sanitization system for the sanitization of a room that overcomes, at least in part, some of the problems identified above.

To mitigate, at least in part, at least one problem associated with the existing technology, there is provided (in accordance with a major aspect) an apparatus. The apparatus includes a sanitization system configured to sanitize, at least in part, an interior space of a room. The sanitization system includes a control system configured to be positioned relative to the interior space of the room. The control system is also configured to be in electrical communication with: (A) a sensor assembly configured to be positioned in the interior space of the room, (B) a door-locking mechanism configured to be operatively connected to a door, in which the door is an entrance to the interior space of the room, and (C) a sanitation-light source configured to be positionable in the interior space of the room.

To mitigate, at least in part, at least one problem associated with the existing technology, there is provided (in accordance with a major aspect) a method. The method is for operating a sanitization system configured to sanitize, at least in part, an interior space of a room, the method comprising: an operation of electrically communicating a control system, in which the control system is positioned relative to the interior space of the room, with: (A) a sensor assembly being configured to be positioned in the interior space of the room, (B) a door-locking mechanism being configured to be operatively connected to a door, in which the door is an entrance to the interior space of the room, and (C) a sanitation-light source being configured to be positionable in the interior space of the room.

Other aspects are identified in the claims. Other aspects and features of the non-limiting embodiments may now become apparent to those skilled in the art upon review of the following detailed description of the non-limiting embodiments with the accompanying drawings. This Summary is provided to introduce concepts in simplified form that are further described below in the Detailed Description. This Summary is not intended to identify key features or essential features of the disclosed subject matter, and is not intended to describe each disclosed embodiment or every implementation of the disclosed subject matter. Many other novel advantages, features, and relationships will become apparent as this description proceeds. The figures and the description that follow more particularly exemplify illustrative embodiments.

BRIEF DESCRIPTION OF THE DRAWINGS

The non-limiting embodiments may be more fully appreciated by reference to the following detailed description of the non-limiting embodiments when taken in conjunction with the accompanying drawings, in which.

Figure 1:
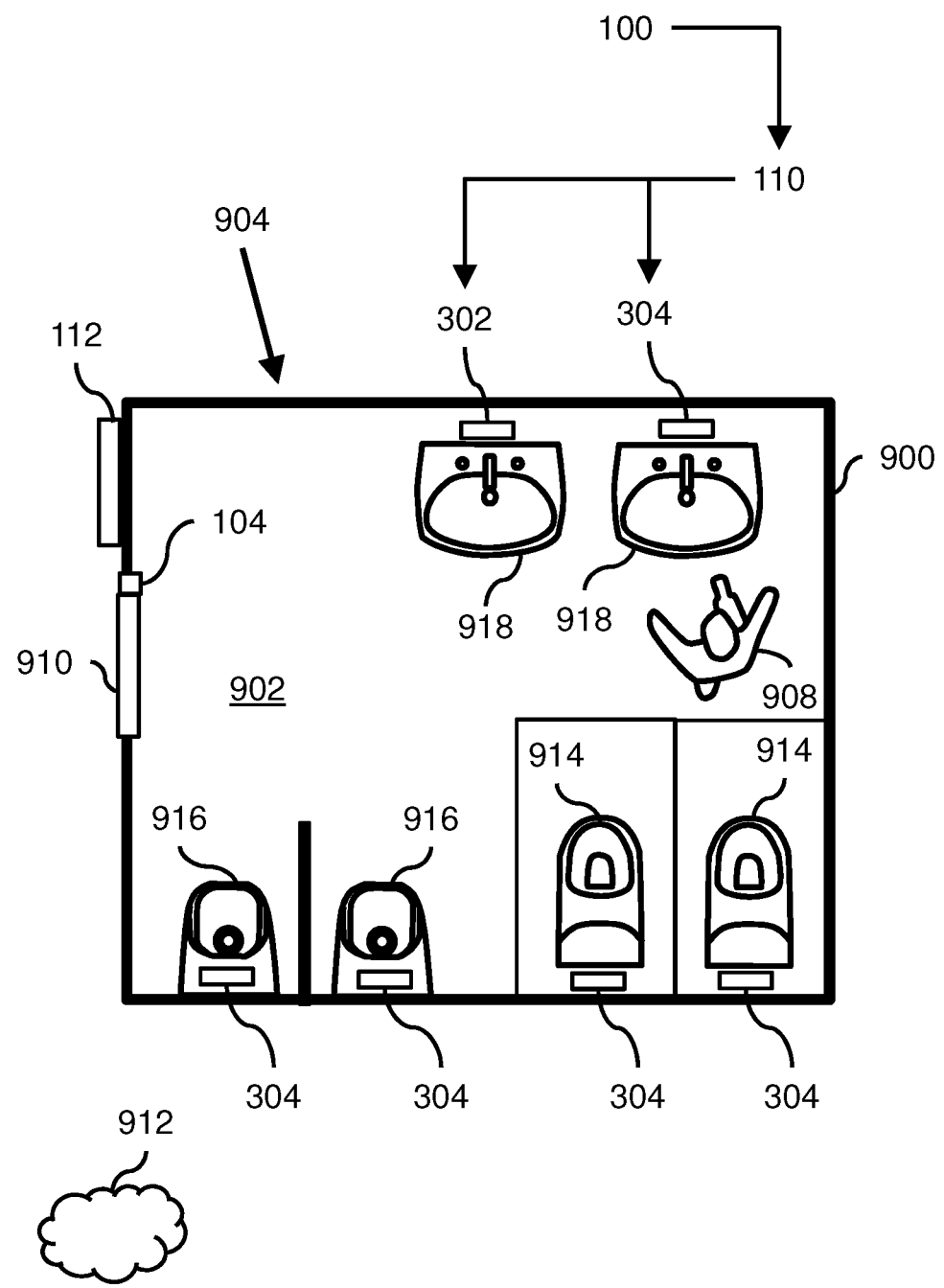
FIG. 1 depicts a top view of an embodiment of a room, in which an embodiment of a sanitization system is installed in association with the room.

The drawings are not necessarily to scale and may be illustrated by phantom lines, diagrammatic representations and fragmentary views. In certain instances, details unnecessary for an understanding of the embodiments (and/or details that render other details difficult to perceive) may have been omitted. Corresponding reference characters indicate corresponding components throughout the several figures of the drawings. Elements in the several figures are illustrated for simplicity and clarity and have not been drawn to scale. The dimensions of some of the elements in the figures may be emphasized relative to other elements for facilitating an understanding of the various disclosed embodiments. In addition, common, but well-understood, elements that are useful or necessary in commercially feasible embodiments are often not depicted to provide a less obstructed view of the embodiments of the present disclosure.

LISTING OF REFERENCE NUMERALS USED IN THE DRAWINGS 100 sanitization system
102 sensor assembly
104 door-locking mechanism
106 sanitation-light source
110 control system
112 display assembly
114 housing assembly
200 processor
202 memory, or non-transitory computer-readable storage medium
204 program
206 wireless transceiver
208 interfacing circuits
212-226 operations
302 primary controller
304 auxiliary controller
312-326 operations
402-416 operations
502-516 operations
900 wall
902 interior space
904 room
906 stationary structure
907 movable structure
908 person
910 door
912 network
914 toilet
916 urinal
918 sink

DETAILED DESCRIPTION OF THE NON-LIMITING EMBODIMENT(S)

The following detailed description is merely exemplary and is not intended to limit the described embodiments or the application and uses of the described embodiments. As used, the word "exemplary" or "illustrative" means "serving as an example, instance, or illustration." Any implementation described as "exemplary" or "illustrative" is not necessarily to be construed as preferred or advantageous over other implementations. All of the implementations described below are exemplary implementations provided to enable persons skilled in the art to make or use the embodiments of the disclosure and are not intended to limit the scope of the disclosure. The scope of may be defined by the claims (in which the claims may be amended during patent examination after filing of this application). For the description, the terms "upper," "lower," "left," "rear," "right," "front," "vertical," "horizontal," and derivatives thereof shall relate to the examples as oriented in the drawings. There is no intention to be bound by any expressed or implied theory in the preceding Technical Field, Background, Summary or the following detailed description. It is also to be understood that the devices and processes illustrated in the attached drawings, and described in the following specification, are exemplary embodiments (examples), aspects and/or concepts defined in the appended claims. Hence, dimensions and other physical characteristics relating to the embodiments disclosed are not to be considered as limiting, unless the claims expressly state otherwise. It is understood that the phrase "at least one" is equivalent to "a". The aspects (examples, alterations, modifications, options, variations, embodiments and any equivalent thereof) are described regarding the drawings. It should be understood that the invention is limited to the subject matter provided by the claims, and that the invention is not limited to the particular aspects depicted and described.

FIG. 1 depicts a top view of an embodiment of a room 904, in which an embodiment of a sanitization system 100 is installed in association with the room 904.

The sanitization system 100 is configured to sanitize, at least in part, an interior space 902 of the room 904. The sanitization system 100, in use, reduces the cost of maintaining the room 904 in a sanitized condition by reducing the labor cost associated with paying someone (a cleaner) for sanitization of the room 904 on a periodic basis. In addition, the cleaner is prone to being inconsistent, while the sanitization system 100 is programmed to be consistent. The sanitization system 100, in use, improves the impression made on users of the room 904 (especially so for the case where the room 904 includes the washroom or restroom of a restaurant, public library, etc.).

Figure 10:
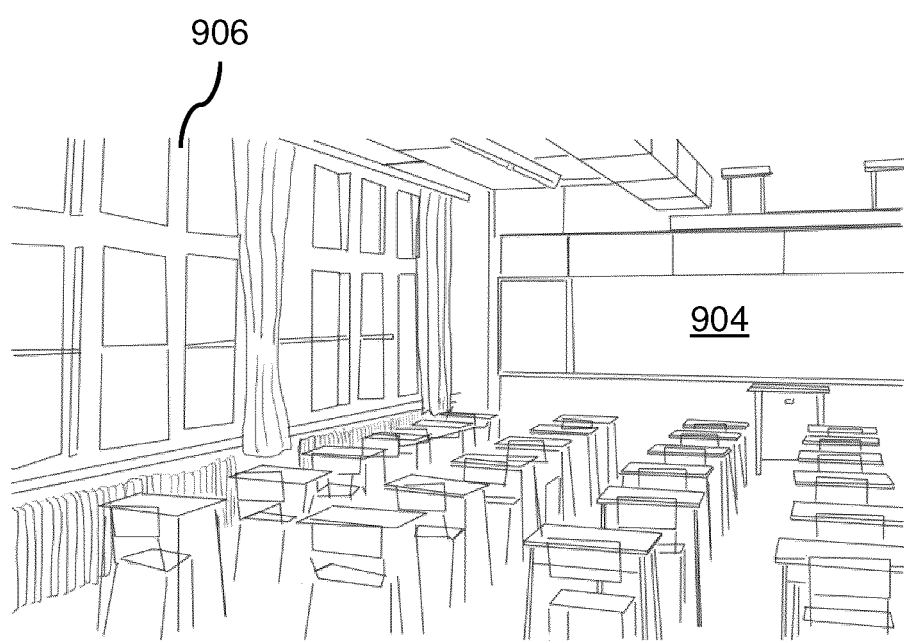
FIG. 10, FIG. 11 and FIG. 12 depict a perspective view (FIG. 10) and top views (FIG. 11 and FIG. 12) of embodiments of the room of FIG. 1.
Figure 11:
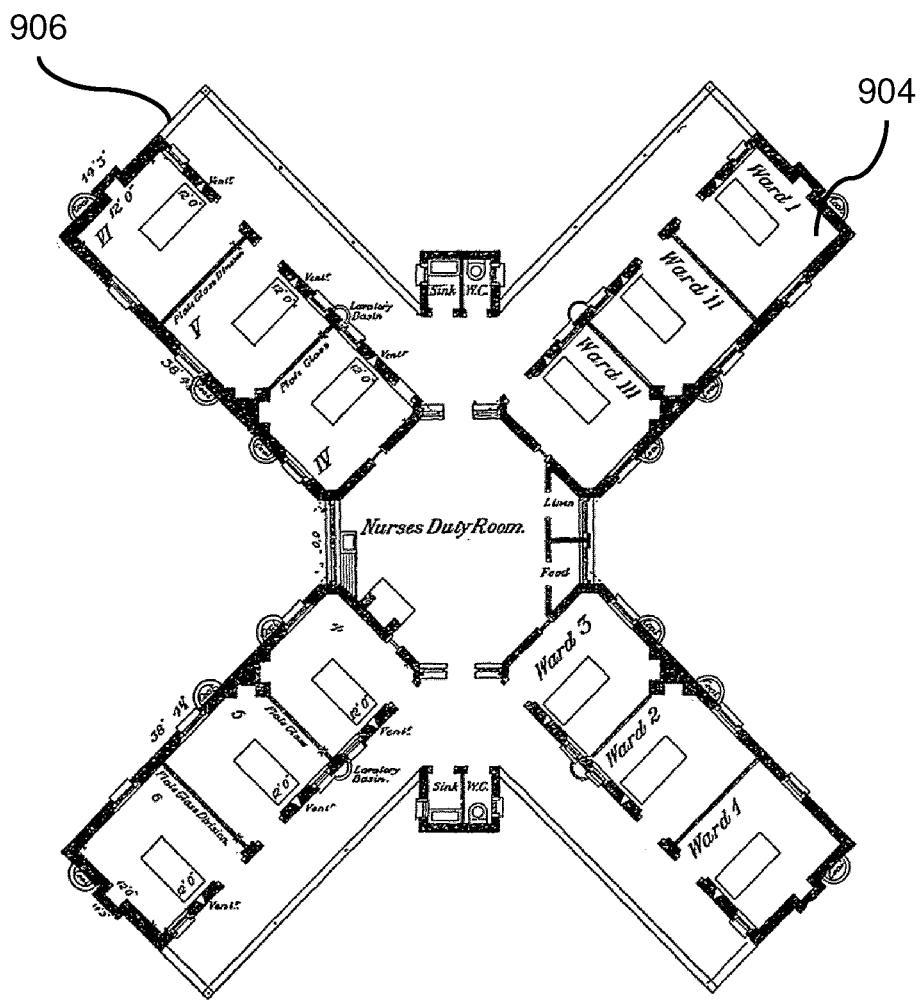
Figure 12:
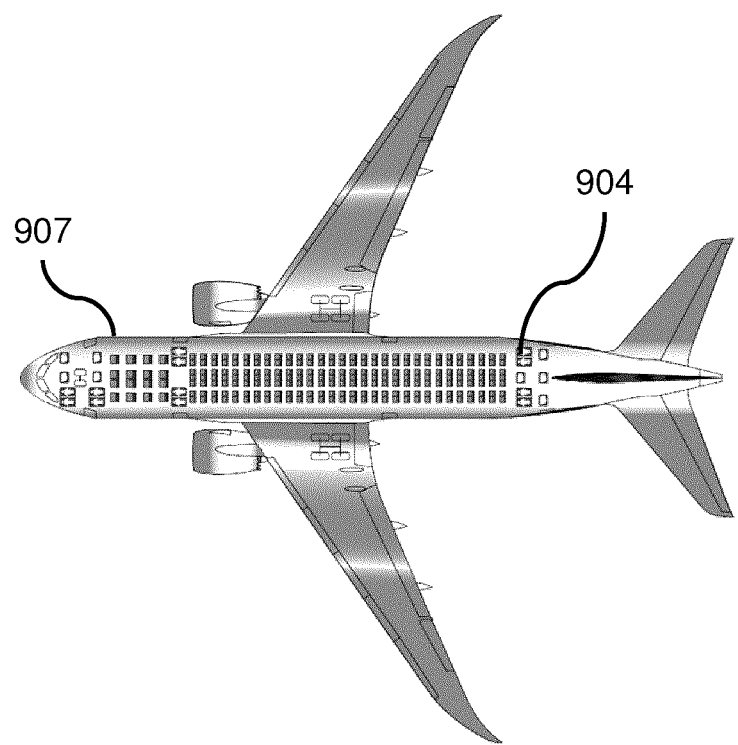

A person 908 (also called a user) is positioned in the interior space 902 of the room 904. The room 904 includes a wall 900 (walls) facing an interior space 902. The room 904 includes outer peripheral walls that define the interior space 902. For instance, the room 904 may include the room of any structure, such as a stationary structure 906 (such as, a building built on a stationary foundation, a hospital, school, etc.), and any equivalent thereof, in which embodiments are depicted in FIG. 10 and FIG. 11. For instance, the room 904 may include the room of a movable structure 907, and any equivalent thereof. The movable structure 907 may be called a vehicle, an aircraft, etc., in which an embodiment is depicted in FIG. 12, etc. A door 910 is installed to the room 904 (the door 910 is installed to a peripheral wall of the room 904), and the door 910 is configured to lead into the interior space 902 of the room 904.

A door-locking mechanism 104 is installed proximate to the door 910. The door-locking mechanism 104 is configured to selectively lock and unlock the door 910.

In accordance with an embodiment, the door-locking mechanism 104 includes the Model Number 350 Narrow Line EMLock (TRADEMARK) door-locking assembly manufactured and/or supplied by SDC (Security Door Controls) based in Camarillo, Calif., USA. The Model Number 350 door-locking assembly provides 1200 pounds holding force and failsafe access control for perimeter and interior doors for building security, and includes sensors indicating magnetic bond and door status, and may be installed on door frame.

Referring to the embodiment as depicted in FIG. 1, the room 904 includes a toilet 914 (at least one or more toilets), a urinal 916 (at least one or more urinals, as may be found in a washroom or a restroom for men), and a sink 918 (at least one or more sinks), all of which are positioned in spaced-apart relationships relative to each other.

Referring to the embodiment as depicted in FIG. 1, the sanitization system 100 includes (and is not limited to) a control system 110. The control system 110 includes (and is not limited to) a primary controller 302 (at least one or more primary controllers 302), and at least one or more auxiliary controllers 304 that are spaced apart from the primary controller 302. The primary controller 302 and the auxiliary controllers 304 are each configured to be positioned relative to (such as, inside) the interior space 902 of the room 904. In accordance with a preferred embodiment, there is one instance of the primary controller 302, and there are several auxiliary controllers 304 that are spaced apart from each other (depending on the size and/or layout of the room 904). Preferably, the primary controller 302 and one or more auxiliary controllers 304 are respectively positioned proximate to a respective user device that is positioned in the room 904. Preferably, each user device requires periodic sanitization. Embodiments of the user device may include (and are not limited to) the toilet 914, the urinal 916, the sink 918, etc.

The primary controller 302 is configured to control the operation of the door-locking mechanism 104 in such a way that the primary controller 302, in use, selectively locks and unlocks the door 910 by selectively activating and deactivating the door-locking mechanism 104 (depending on predetermined conditions associated with the room 904).

Generally, the control system 110 (or the primary controller 302) is configured to: (A) determine whether a predetermined time (also called a time delay) has lapsed since the last time the room 904 was cleaned or sanitized; (B) determine whether the room 904 is not occupied (by using appropriate sensors); (C) lock the door 910 (via actuation of the door-locking mechanism 104) for the case where the control system 110 determined that (a) the predetermined time has lapsed since the last time the room 904 was cleaned or sanitized, and (b) the room 904 is not occupied (by using appropriate sensors); (D) initialize sanitization of the interior space 902 of the room 904 (by using appropriate sanitization devices) for the case where the control system 110 had determined that (a) the predetermined time has lapsed since the last time the room 904 was cleaned or sanitized, and (b) the room 904 is not occupied (by using appropriate sensors); and (E) unlock the door 910 for the case where sanitization of the room 904 has been completed.

Preferably, the primary controller 302 and the auxiliary controllers 304 are configured to electrically communicate with (interact with) a network 912. Preferably, the auxiliary controllers 304 are configured to electrically communicate with (interact with) the primary controller 302 via the network 912. The network 912 may include a secured network or an unsecured network (provided the controllers use security techniques, such as a password, etc., to ensure secured communications, thereby avoiding unintended or unwanted tampering of the control system 110, the primary controller 302 and/or the auxiliary controller 304). The network 912 may include a wide-area network or a local-area network, etc. Alternatively, the auxiliary controllers 304 are configured to electrically communicate with (interact with) each other via the network 912 (if desired). For instance, for the case where one of the auxiliary controllers 304, in use, fails or becomes inoperative, any auxiliary controllers 304, which are operative, may then alert the primary controller 302 of the inoperative auxiliary controller 304. For instance, for the case where the primary controller 302 becomes in-operative, a selected one of the auxiliary controllers 304 can operate as the default primary controller 302 in place of the inoperative primary controller 302, etc.

Figure 2:
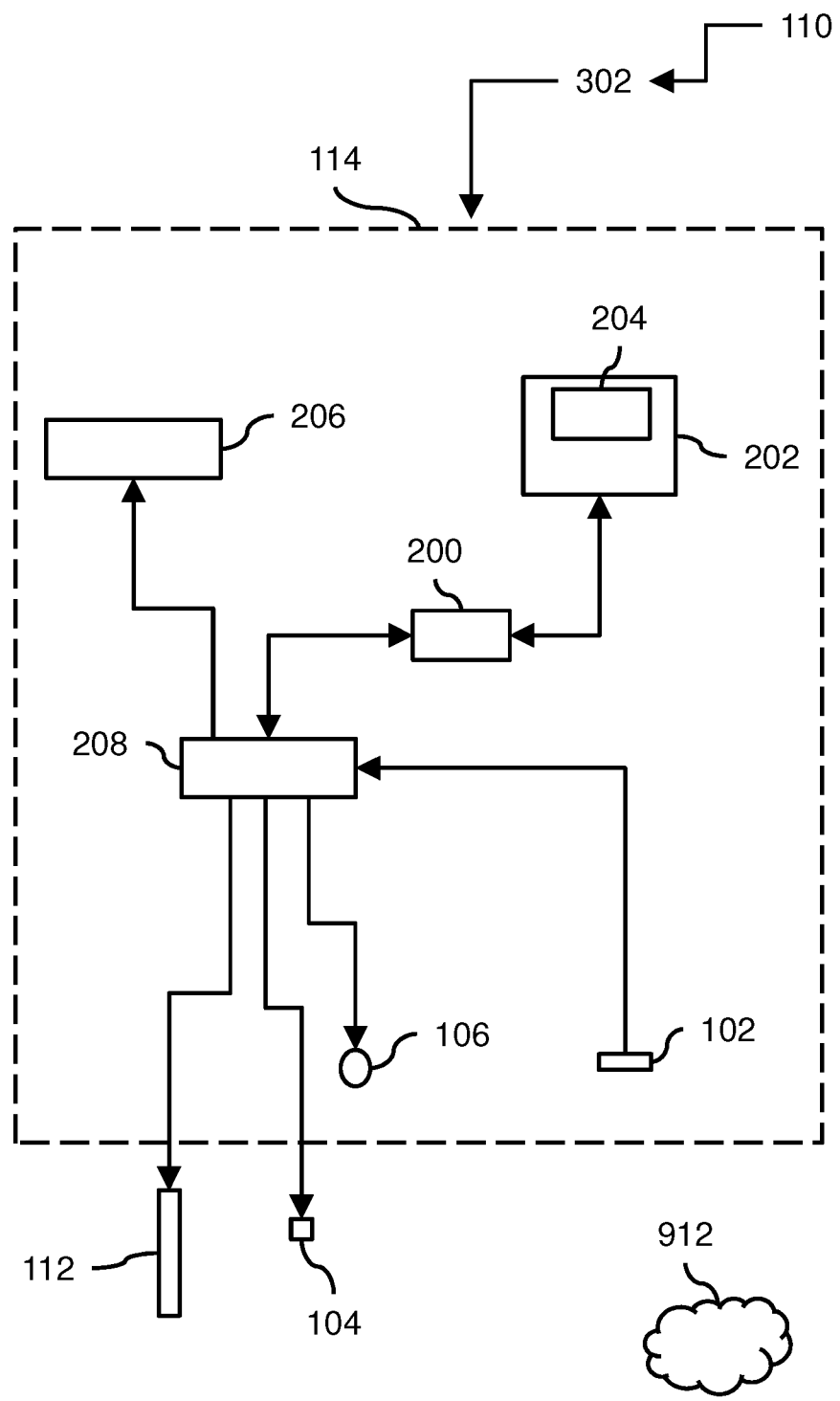
FIG. 2 and FIG. 3 depict a first schematic view (FIG. 2) and a second schematic view (FIG. 3) of the embodiments of the sanitization system of FIG. 1.
Figure 3:
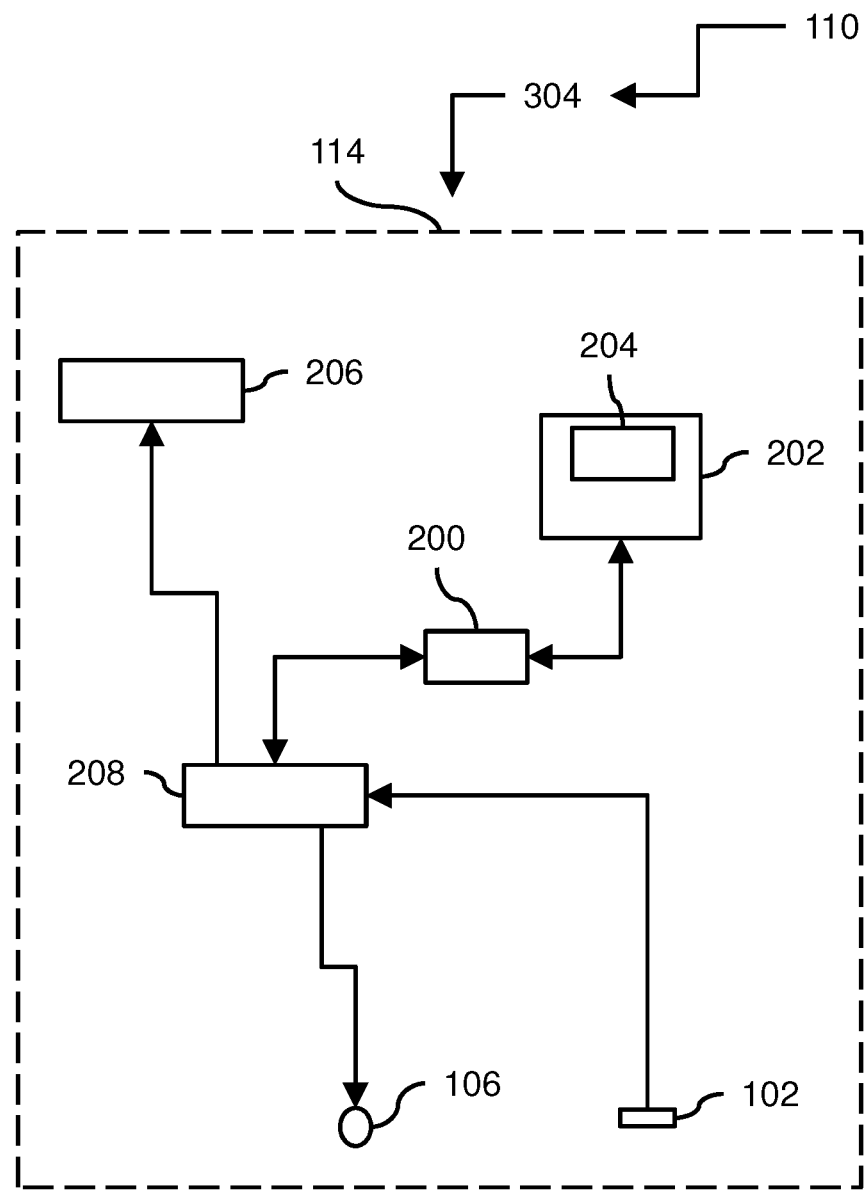
Figure 3:
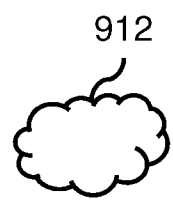

Referring to the embodiments as depicted in FIG. 2 and FIG. 3, the control system 110 (such as, the primary controller 302 and/or the auxiliary controller 304) is further configured to be housed and supported by the housing assembly 114, in which the housing assembly 114 is configured to be positionable (such as, affixed to a wall 900 facing the interior space 902) in the interior space 902 of the room 904.

Referring to the embodiments as depicted in FIG. 1 the control system 110 (such as, the primary controller 302 and/or the auxiliary controller 304) includes at least two or more instances of the control system 110 that are positioned in (mounted in) spaced-apart positions in the room 904. Each of the at least two or more instances the control system 110 is configured to be in electrical communication with each other (wired or wirelessly) via a network 912 (wired network, wireless network, or hybrid wired and wireless network). The at least two or more instances of the housing assembly 114 are positioned in (mounted in) spaced-apart positions in the room 904. Each of the at least two or more instances of the housing assembly 114 respectively include a respective instance of the control system 110, each of which is configured to be in electrical communication with each other (wired or wirelessly) via the network 912.

Referring to the embodiment as depicted in FIG. 1, the control system 110 is further configured to be in electrical communication with a display assembly 112.

The control system 110 is further configured to transmit a display signal to the display assembly 112.

In accordance with an embodiment, the display assembly 112 includes the Model Number PICADILLO-35T touch screen display supplied and/or manufactured by 4D Systems Pty Ltd based on Minchinbury, Australia, and provides a 3.5 inch touch screen with an onboard controller for running user software.

For instance, the control system 110 may be configured to be operatively coupled with (electrically connected with) any one of a hard wire and/or a wireless-network connection, etc., and any equivalent thereof. This is done in such a way that the control system 110, in use, transmits an occupancy-indication signal to the display assembly 112. The occupancy-indication signal is configured to indicate an occupation status of the room 904. For instance, the occupation status of the room 904 may include any one of (A) the room 904 is being cleaned, (B) the time to complete the cleaning of the room 904, and/or (C) the room 904 is available for usage, etc., and any equivalent thereof.

Preferably, the primary controller 302, is configured to be in electrical communication with the display assembly 112 (for instance, via the network 912).

The display assembly 112 is positioned outside of the room 904 (that is, not positioned in the interior space 902). Preferably, the display assembly 112 is mounted (affixed) to the wall, and is mounted proximate to the door 910 (adjacent to the door 910 or on the exterior of the door 910, etc.).

FIG. 2 and FIG. 3 depict a first schematic view (FIG. 2) and a second schematic view (FIG. 3) of the embodiments of the sanitization system 100 of FIG. 1.

The primary controller 302 is supported by a housing assembly 114 (as depicted in FIG. 2), and the auxiliary controller 304 is also supported by another instance of the housing assembly 114 (as depicted in FIG. 3).

Referring to the embodiment as depicted in FIG. 2, the primary controller 302 includes a sensor assembly 102 (preferably a single sensor assembly) and a sanitation-light source 106 (preferably a single sanitation-light source), both of which are supported by (integrated with) and mounted to the housing assembly 114 (this embodiment may provide for reduced cost and/or time for installation of the sanitization system 100 in the room 904, as depicted in FIG. 1).

For instance, for the case where the sanitization system 100 is to be deployed (installed) in a residential bathroom of a residential home (in which there is expected a relatively simple set-up of a single sink and a single toilet, or a single sink, a single toilet and a single shower or single bath), the sanitization system 100 is not deployed with the display assembly 112 because once the door 910 is locked, the user expects that the sanitization system 100 is operating and there is simply no need for the display assembly 112. The display assembly 112, in this case, may be optional, and/or the display assembly 112 may include a relatively simple set-up, such as a lamp that turns ON and OFF, if so desired, etc.

The sensor assembly 102 may include, for instance, a motion sensor, a heat sensor, or a combination thereof.

In accordance with an embodiment, the sensor assembly 102 includes the Model Number AMN31111 sensor assembly supplied by and/or manufactured by Panasonic Electric Works, based in Ottobrunn, Germany, and includes a passive infrared sensor configured to detect human presence at a range of about five meters.

The sanitation-light source 106 may include an ultra violet emitting lamp (UV-light source) configured to emit ultra violet light of any suitable frequency, and any equivalent thereof. The sanitation-light source 106 may include LED (Light Emitting Diodes) configured to emit ultra violet light.

In accordance with an embodiment, the sanitation-light source 106 includes the Model Number S-S35D-F2-275-01-3-180 UV LED light assembly (for relatively higher power requirements) supplied by and/or manufactured by Sensor Electronic Technologies based in Columbia, S.C., USA. In accordance with an embodiment, the sanitation-light source 106 includes the Model Number S-S35B-E1-275-01-2-110 UV LED light assembly (for relatively lower power requirements) supplied by and/or manufactured by Sensor Electronic Technologies based in Columbia, S.C., USA.

Referring to the embodiment as depicted in FIG. 3, the auxiliary controller 304 includes the sensor assembly 102 (preferably a single sensor assembly) and the sanitation-light source 106 (preferably a single sanitation-light source), both of which are supported by (integrated with) and mounted to the housing assembly 114 (this embodiment may provide for reduced time and/or cost for installation of the sanitization system 100 in the room 904, as depicted in FIG. 1).

The auxiliary controller 304 does not have to be configured to be in electrical communication (operative communication) with the display assembly 112 and the door-locking mechanism 104. Alternatively, the auxiliary controller 304 is configured to provide back-up support for the primary controller 302 for the case where the primary controller 302, in use, fails to be operative, and the auxiliary controller 304 is configured to be in electrical communication (operative communication) with the display assembly 112 and the door-locking mechanism 104.

Referring to the embodiments as depicted in FIG. 2 and FIG. 3, the control system 110. Referring to FIG. 2, the control system 110 includes the primary controller 302. Referring to FIG. 3, the control system 110 includes the auxiliary controller 304. The control system 110 includes a processor 200, and a non-transitory computer-readable storage medium 202 (hereafter referred to as the memory 202) that is electrically connected to the processor 200. The memory 202 includes (tangibly embodies) a program 204 (also called computer-executable instructions). The program 204 is executable by the processor 200 in such a way that the processor 200 is urged to perform operations. An equivalent of the combination of the processor 200, the memory 202 and the program 204 is an application-specific integrated circuit (ASIC, or any equivalent thereof), which is an integrated circuit (IC) customized for a particular use, or for general-purpose use.

In accordance with an embodiment, the processor 200 includes the Model Number PIC32MM0064GPL036 controller assembly supplied by and/or manufactured by Microchip based in Chandler, Ariz., USA.

The program 204 may be called computer software, or simply software, also known as a computer program. Computer software includes all computer programs regardless of their architecture; for example, executable files, libraries and scripts are computer software. Computer software includes clearly defined processor-executable instructions that, upon execution, instruct hardware (the processor 200) to perform the predetermined tasks for which the processor 200 is designed. Software is tangibly stored in computer memory. At the lowest level, executable code consists of machine language instructions specific to an individual processor, such as a central processing unit (CPU). A machine language consists of groups of binary values signifying processor instructions that change the state of the computer from its preceding state. For example, an instruction may change the value stored in a particular storage location inside the computer—an effect that is not directly observable to the user. An instruction may also (indirectly) cause something to appear on a display of the computer system—a state change which should be visible to the user. The processor carries out the instructions in the order in which they are provided, unless it is instructed to "jump" to a different instruction, or interrupted. Software is usually written in high-level programming languages that are easier and more efficient for humans to use (closer to natural language) than machine language. High-level languages are compiled or interpreted into machine language object code. Software may also be written in a low-level assembly language, essentially, a vaguely mnemonic representation of a machine language using a natural language alphabet. Assembly language is converted into object code via an assembler. Application software is all the computer software that causes a computer to perform useful tasks beyond the running of the computer itself. A specific instance of such software is called a software application, application program, application or app. The term is used to contrast such software with system software, which manages and integrates a computer's capabilities but does not directly perform tasks that benefit the user. The system software serves the application, which in turn serves the user.

The memory 202 may include any type of computer-readable memory or computer-read/writable memory device.

Preferably, the control system 110 is also configured to electrically connect to a wireless transceiver 206 that is configured to receive and transmit signals wirelessly with the network 912.

Preferably, the control system 110 (such as, the primary controller 302 of FIG. 2 or the auxiliary controller 304 of FIG. 3) is configured to be in electrical communication with the interfacing circuits 208 (known and not discussed here in any detail). The interfacing circuits 208 are configured to interface with sensor assembly 102, the door-locking mechanism 104, the sanitation-light source 106, the display assembly 112, and the wireless transceiver 206 with the control system 110 (such as, the primary controller 302 of FIG. 2 or the auxiliary controller 304 of FIG. 3).

Referring to the embodiments as depicted in FIG. 2 and FIG. 3, an apparatus includes (and is not limited to) the sanitization system 100. The sanitization system 100 is configured to sanitize, at least in part, the interior space 902 of the room 904 (such as of the stationary structure 906, of which an embodiment is depicted in FIG. 10 or FIG. 11, or of the movable structure 907, of which an embodiment is depicted in FIG. 12). The sanitization system 100 includes (and is not limited to) the control system 110 configured to be positioned relative to (such as, positioned in or positioned outside of) the interior space 902 of the room 904. The control system 110 is also configured to be in electrical communication with (operatively coupled with or connected with either a hard wire or via a wireless connection): (A) the sensor assembly 102 configured to be positioned in the interior space 902 of the room 904, (B) the door-locking mechanism 104 configured to be operatively connected to the door 910, in which the door 910 is an entrance to the interior space 902 of the room 904, and (C) the sanitation-light source 106 configured to be positionable in the interior space 902 of the room 904.

Referring to the embodiments as depicted in FIG. 2 and FIG. 3, there is provided a method of operating the sanitization system 100 configured to sanitize, at least in part, the interior space 902 of the room 904. The method includes (and is not limited to) an operation of electrically communicating a control system 110, in which the control system 110 is positioned relative to the interior space 902 of the room 904, with: (A) a sensor assembly 102 being configured to be positioned in the interior space 902 of the room 904, (B) a door-locking mechanism 104 being configured to be operatively connected to a door 910, in which the door 910 is an entrance to the interior space 902 of the room 904, and (C) a sanitation-light source 106 being configured to be positionable in the interior space 902 of the room 904.

Referring to the embodiment as depicted in FIG. 2, the sanitization system 100 includes (and is not limited to) the primary controller 302 configured to be positioned relative to (such as, positioned in or positioned outside of) the interior space 902 of the room 904. The primary controller 302 is also configured to be in electrical communication with (operatively coupled with or connected with either a hard wire or via a wireless connection): (A) the sensor assembly 102 configured to be positioned in the interior space 902 of the room 904, (B) the door-locking mechanism 104 configured to be operatively connected to the door 910, in which the door 910 is an entrance to (such as, leads into) the interior space 902 of the room 904, and (C) the sanitation-light source 106 configured to be positionable in the interior space 902 of the room 904.

Referring to the embodiment as depicted in FIG. 3, the sanitization system 100 includes (and is not limited to) the auxiliary controller 304 configured to be positioned relative to (such as, positioned in or positioned outside of) the interior space 902 of the room 904. The auxiliary controller 304 is also configured to be in electrical communication with (operatively coupled with or connected with either a hard wire or via a wireless connection): (A) the sensor assembly 102 configured to be positioned in the interior space 902 of the room 904, (B) the door-locking mechanism 104 configured to be operatively connected to the door 910, in which the door 910 is an entrance to the interior space 902 of the room 904, and (C) the sanitation-light source 106 configured to be positionable in the interior space 902 of the room 904.

Referring to the embodiments as depicted in FIG. 1, FIG. 2 and FIG. 3, the control system 110 (such as, the primary controller 302 and/or the auxiliary controller 304) is further configured to receive a presence status indicator signal from the sensor assembly 102 once the sensor assembly 102 detects the presence of a person 908 located in a predefined portion of (preferably all of) the interior space 902 of the room 904. The control system 110 (such as, the primary controller 302 and/or the auxiliary controller 304) is further configured to transmit a door-control signal to the door-locking mechanism 104 in response to the control system 110 receiving the presence status indicator signal from the sensor assembly 102. The control system 110 (such as, the primary controller 302 and/or the auxiliary controller 304) is further configured to transmit a light-source control signal to the sanitation-light source 106 in response to the control system 110 transmitting the door-control signal to the door-locking mechanism 104.

Referring to the embodiments as depicted in FIG. 1, FIG. 2 and FIG. 3, the control system 110 (such as, the primary controller 302 and/or the auxiliary controller 304) is further configured to receive a presence status indicator signal from the sensor assembly 102. The sensor assembly 102 is further configured to: (A) detect, at least in part, the presence of a person 908 located in a predefined portion of (preferably all of) the interior space 902 of the room 904, and (B) transmit the presence status indicator signal to the control system 110 in response to the sensor assembly 102 detecting the presence of the person 908 located in the interior space 902.

Referring to the embodiments as depicted in FIG. 1, FIG. 2 and FIG. 3, the control system 110 (such as, the primary controller 302 and/or the auxiliary controller 304) is further configured to transmit a door-control signal to the door-locking mechanism 104. The door-locking mechanism 104 is further configured to selectively lock the door 910 in response to the door-locking mechanism 104, in use, receiving the door-control signal from the control system 110 in such a way that the door-locking mechanism 104, in use, selectively locks and unlocks (such as magnetically locking and unlocking) the door 910.

Referring to the embodiments as depicted in FIG. 1, FIG. 2 and FIG. 3, the control system 110 (such as, the primary controller 302 and/or the auxiliary controller 304) is further configured to transmit a light-source control signal to the sanitation-light source 106. The sanitation-light source 106 is further configured to receive the light-source control signal from the control system 110, in which the light-source control signal, in use, selectively turns ON and OFF the sanitation-light source 106. The sanitation-light source 106 is further configured to selectively emit a sanitation light into the interior space 902 of the room 904, in response to the sanitation-light source 106 receiving the light-source control signal. This is done in such a way that the sanitation light, which is emitted by the sanitation-light source 106 during use, sanitizes, at least in part, the interior space 902 of the room 904.

Referring to the embodiments as depicted in FIG. 1, FIG. 2 and FIG. 3, the control system 110 (such as, the primary controller 302 and/or the auxiliary controller 304) is further configured to transmit a door-control signal to the door-locking mechanism 104, for the case where the control system 110 receives a presence status indicator signal, from the sensor assembly 102, in which the presence status indicator signal indicates that the room 904 is occupied by a person 908 positioned in the interior space 902 of the room 904, and in which the door-control signal, in use, keeps the door 910 in an unlocked state. The control system 110 is further configured to monitor and ensure that (A) the sanitation-light source 106 remains in an OFF state, and (B) the door-locking mechanism 104 does not lock the door 910.

Referring to the embodiments as depicted in FIG. 1, FIG. 2 and FIG. 3, the control system 110 (such as, the primary controller 302 and/or the auxiliary controller 304) is further configured to transmit the door-control signal to the door-locking mechanism 104, for the case where the control system 110 receives the presence status indicator signal, from the sensor assembly 102, in which the presence status indicator signal indicates that the room 904 is NOT occupied by anyone that is positioned in a predefined portion of (preferably all of) the interior space 902 of the room 904, and in which the door-control signal, in use, keeps the door 910 in a locked state.

Referring to the embodiments as depicted in FIG. 1, FIG. 2 and FIG. 3, the control system 110 (such as, the primary controller 302 and/or the auxiliary controller 304) is further configured to monitor and ensure that (A) the door-locking mechanism 104, in use, maintains the door 910 in a locked stated for the case where the control system 110 determines that the entirety of the room 904 is empty and unoccupied by anyone, and (B) the sanitation-light source 106 is turned ON for a predetermined period of time.

Referring to the embodiments as depicted in FIG. 1, FIG. 2 and FIG. 3, the control system 110 (such as, the primary controller 302 and/or the auxiliary controller 304) is further configured to (A) turn OFF, once the predetermined period of time has lapsed, and (B) transmit, once the predetermined period of time is lapsed and the sanitation-light source 106 has turned OFF, the door-control signal to the door-locking mechanism 104. This is done in such a way that the door-control signal, in use, urges the door-locking mechanism 104 to unlock the door 910.

Referring to the embodiments as depicted in FIG. 1, FIG. 2 and FIG. 3, the control system 110 (such as, the primary controller 302 and/or the auxiliary controller 304) is further configured to control the operation of the sanitation-light source 106 once the control system 110 is electrically connected to the sanitation-light source 106, and the sanitation-light source 106 receives electrical power.

Referring to the embodiments as depicted in FIG. 1, FIG. 2 and FIG. 3, the control system 110 (such as, the primary controller 302 and/or the auxiliary controller 304) is further configured to (A) receive a presence status indicator signal from the sensor assembly 102, and (B) transmit a door-control signal to the door-locking mechanism 104. This is done in such a way that the door-control signal, in use, urges the door-locking mechanism 104 to lock the door 910 for the case where the sensor assembly 102 does not detect, at least in part, the presence of the person 908 positioned in the interior space 902 of the room 904.

Referring to the embodiments as depicted in FIG. 1, FIG. 2 and FIG. 3, the control system 110 (such as, the primary controller 302 and/or the auxiliary controller 304) is further configured to turn ON the sanitation-light source 106 for the case where: (A) the control system 110 transmitted a door-control signal to the door-locking mechanism 104, and (B) the control system 110 did not receive a presence status indicator signal from the sensor assembly 102, in which the presence status indicator signal indicates no detection of the presence of the person 908 positioned in the interior space 902 of the room 904.

Referring to the embodiments as depicted in FIG. 1, FIG. 2 and FIG. 3, the control system 110 (such as, the primary controller 302 and/or the auxiliary controller 304) is further configured to turn OFF the sanitation-light source 106 (once a predetermined time duration has lapsed after the control system 110 has turned ON the sanitation-light source 106).

Referring to the embodiments as depicted in FIG. 1, FIG. 2 and FIG. 3, the control system 110 (such as, the primary controller 302 and/or the auxiliary controller 304) is further configured to transmit a door-control signal to the door-locking mechanism 104 in such a way that the door-control signal (in use) urges the door-locking mechanism 104 to unlock the door 910.

Referring to the embodiments as depicted in FIG. 1, FIG. 2 and FIG. 3, the control system 110 (such as, the primary controller 302 and/or the auxiliary controller 304) is further configured to cooperate with the sensor assembly 102 that is configured to be supported by a housing assembly 114 in such a way that the sensor assembly 102: (A) is positionable in the interior space 902 of the room 904, and (B) faces, in use, the interior space 902 of the room 904 (once the housing assembly 114 is positioned in (such as, affixed to a wall 900) and faces the interior space 902 of the room 904).

Referring to the embodiments as depicted in FIG. 1, FIG. 2 and FIG. 3, the control system 110 (such as, the primary controller 302 and/or the auxiliary controller 304) is further configured to cooperate with the sanitation-light source 106 that is configured to be supported by a housing assembly 114 in such a way that the sanitation-light source 106: (A) is spaced apart from the sensor assembly 102, (B) is positionable in the interior space 902 of the room 904, and (C) faces, in use, the interior space 902 of the room 904 once the housing assembly 114 is positioned in (such as, affixed to a wall 900), and face the interior space 902 of the room 904.

Referring to the embodiments as depicted in FIG. 1, FIG. 2 and FIG. 3, the control system 110 (such as, the primary controller 302 and/or the auxiliary controller 304) is further configured to cooperate with the sensor assembly 102 that is configured to be supported by a housing assembly 114 in such a way that (A) the sensor assembly 102 is positionable in the interior space 902 of the room 904, and (B) the sensor assembly 102, in use, faces the interior space 902 of the room 904 once the housing assembly 114 is positioned in (such as, affixed to a wall 900) and faces the interior space 902 of the room 904.

Referring to the embodiments as depicted in FIG. 1, FIG. 2 and FIG. 3, the control system 110 (such as, the primary controller 302 and/or the auxiliary controller 304) is further configured to cooperate with the sanitation-light source 106 that is configured to be supported by the housing assembly 114 in such a way that (A) the sanitation-light source 106 is spaced apart from the sensor assembly 102, (B) the sanitation-light source 106 is positionable in the interior space 902 of the room 904, and (C) the sanitation-light source 106, in use, faces the interior space 902 of the room 904 once the housing assembly 114 is positioned in (such as, affixed to the wall 900 facing) the interior space 902 of the room 904.

In accordance with the embodiments as depicted in FIG. 1, FIG. 2 and FIG. 3, an apparatus includes (and is not limited to) the sanitization system 100 configured to sanitize, at least in part, an interior space 902 of a room 904 (such as that of a stationary structure 906 or of a movable structure 907). The sanitization system 100 includes (and is not limited to) a synergistic combination of: (A) the sensor assembly 102 configured to be positioned in the interior space 902 of the room 904, (B) the sanitation-light source 106 configured to be positionable in the interior space 902 of the room 904, (C) the control system 110 (such as, the primary controller 302 or the auxiliary controller 304), and (D) the housing assembly 114 configured to house and support the control system 110, the sensor assembly 102, and the sanitation-light source 106. The control system 110 is configured to: (A) be positioned relative to (such as, positioned in or outside of) the interior space 902 of the room 904, and (B) be in electrical communication with (operatively coupled with or connected with via a wire or a wireless connection) to: (a) the sensor assembly 102, (b) the sanitation-light source 106, (c) the door-locking mechanism 104 configured to be operatively connected to a door 910, in which the door 910 is an entrance to the interior space 902 of the room 904, and (d) the display assembly 112 positioned outside of the room 904.

Figure 4:
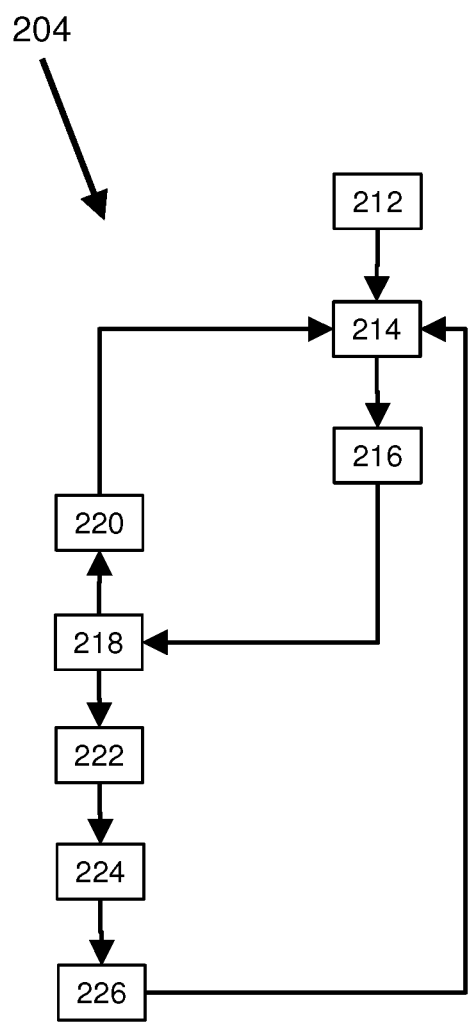
FIG. 4 and FIG. 5 depict a first flow chart (FIG. 4) and a second flow chart (FIG. 5) indicating operations of the embodiments of the sanitization system of FIG. 2 and FIG. 3, respectively.
Figure 5:
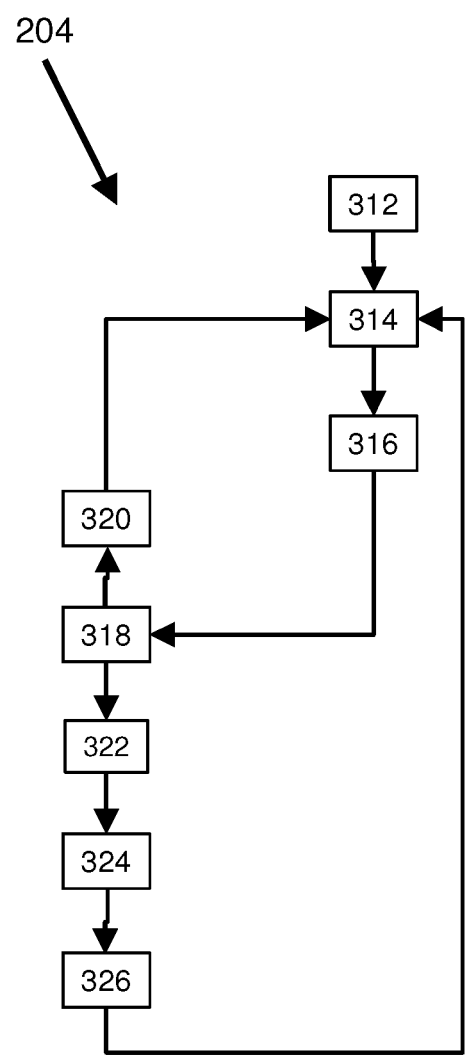

FIG. 4 and FIG. 5 depict a first flow chart (FIG. 4) and a second flow chart (FIG. 5) indicating operations of the embodiments of the sanitization system 100 of FIG. 2 and FIG. 3, respectively.

Referring to the embodiment as depicted in FIG. 4, the program 204 is schematically depicted as a flow chart of operations. The operations of the program 204 are described with sufficient details so that a person skilled in the art can form (prepare) the programmed instructions using a high-level computer program, which may then be converted into executable-coded instructions configured to direct the processor 200 (of the primary controller 302) to perform various operations (as described below).

Operation 212 includes directing the processor 200 of the primary controller 302 to operate in an initialization mode (also called a reset mode), in which the primary controller 302 performs the following operations: operations 212A to 212F. Once operation 212 is completed, operational control is transferred to operation 214.

Operation 212A includes deactivating the sanitation-light source 106 associated with the primary controller 302; this is done in such a way that the sanitation-light source 106 becomes deactivated, and the sanitation light from the sanitation-light source 106 (which is associated with or connected to and controllable by the primary controller 302) is not exposed to anyone positioned in the room 904.

Operation 212B includes identifying the auxiliary controllers 304 that are deployed in the room 904 by communicating or exchanging inquiry signals and confirmation signals via the network 912 with any of the auxiliary controllers 304 that may be deployed and activated in the room 904.

Operation 212C includes transmitting, to each of the auxiliary controllers 304 via the network 912, a deactivation request signal configured to deactivate the sanitation-light sources 106 (which are associated with or connected to at least one of the auxiliary controllers 304 deployed in the room 904, in which this is an indirect manner for deactivation); this is done in such a way that the sanitation-light sources 106 become deactivated, and the sanitation light (which is emitted from the sanitation-light sources 106, and the sanitation-light sources 106 are respectively associated with each of the auxiliary controllers 304) is not exposed to anyone that may be positioned in the room 904.

Operation 212D includes (for the case where any sanitation-light sources 106, which are deployed in the room 904, are not operational or not responsive to the deactivation command issued by the primary controller 302) transmitting the display signal to the display assembly 112. This is done in such a way that the display assembly 112, in use, displays an error code. The error code indicates that at least one or more of the sanitation-light sources 106, which are deployed in the room 904, may be defective and may need replacement, etc.

Operation 212E includes (for the case where each sanitation-light source 106 deployed in the room 904 are deactivated or confirmed to be deactivated) transmitting the door-control signal to the door-locking mechanism 104. The door-control signal is configured to deactivate the door-locking mechanism 104. This operation places the door-locking mechanism 104 in the unlocked state. The door-locking mechanism 104 is controllable and is associated with the primary controller 302. This operation is done in such a way that the door 910 may be opened by anyone, and the room 904 may be occupied since all of the sanitation-light sources 106 (which are deployed in the room 904) are not activated.

Operation 212F includes (for the case where the door-locking mechanism 104 has been deactivated) transmitting the display signal to the display assembly 112 (in which the display assembly 112 is controllable and is associated with the primary controller 302); this is done in such a way that the display assembly 112, in use, displays and indicates that the room 904 is available (for usage).

Operation 214 includes directing the processor 200 of the primary controller 302 to execute the following operations: operations 214A to 214D. Once operation 214 is completed, operational control is transferred to operation 216.

Operation 214A includes periodically monitoring and receiving (in a direct manner) the occupancy-indication signal (which is received from the sensor assembly 102 associated with the primary controller 302).

Operation 214B includes periodically monitoring and receiving (in an indirect manner) the occupancy-indication signals provided by all of the auxiliary controllers 304 that are deployed in the room 904. The occupancy-indication signals are received from each sensor assembly 102 (which is associated with a respective auxiliary controller 304 deployed in the room 904).

Operation 214C includes checking (either directly or indirectly via the auxiliary controller 304) whether the room 904 is occupied. Occupancy is based on any occupancy-indication signal received from any sensor assembly 102 (which is deployed in the room 904, regardless of whether the sensor assembly 102 is associated with the primary controller 302 or the auxiliary controllers 304) indicates that there is at least one (or more) persons 908 present in the room 904.

Operation 214D includes (for the case where the room 904 is occupied by at least one or more persons 908): (A) continuing to ensure that each of the sanitation-light sources 106 (the sanitation-light sources 106 that are deployed in the room 904) remain deactivated, and (B) continuing to ensure that the door-locking mechanism 104 remains in the unlocked state (because the room 904 remains occupied).

Operation 216 includes directing the processor 200 of the primary controller 302 to execute the following operations: operations 216A to 216B. Once operation 216 is completed, operational control is transferred to operation 218.

Operation 216A includes activating the door-locking mechanism 104 (so that the door-locking mechanism 104 is placed in the locked state); this is done in such a way that the door-locking mechanism 104, in use, locks the room 904, and prevents access to the room 904 to any users or persons (for the case where the primary controller 302 has determined that the room 904 is unoccupied). This is based on the primary controller 302 making a determination that all of the occupancy-indication signals (from each sensor assembly 102) indicate that there are no persons present in the room 904. Therefore, the room 904 is presently unoccupied, regardless of whether the sensor assembly 102 is associated with the primary controller 302 or any auxiliary controller 304.

An option (variation) for operation 216A may include determining whether a predetermined time (also called a time delay) has lapsed since the last time the room 904 was cleaned or sanitized. If the determination indicates that the predetermined time has lapsed since the last time the room 904 was cleaned or sanitized, then operation 216A includes activating the door-locking mechanism 104 (so that the door-locking mechanism 104 is placed in the locked state); this is done in such a way that the door-locking mechanism 104, in use, locks the room 904, and prevents access to the room 904 by any users or persons (for the case where the primary controller 302 determined that the room 904 was unoccupied based on the primary controller 302 determining that all of the occupancy-indication signals from each sensor assembly 102 indicating that there were no persons present in the room 904).

Operation 216B includes transmitting the display signal to the display assembly 112 in such a way that the display assembly 112, in use, displays an update status; this is done in such a way that the display assembly 112 indicates that the room 904 is being sanitized, and that the room 904 will be available for use at a later time (with an indication showing an amount of wait time, etc.).

Operation 218 includes directing the processor 200 of the primary controller 302 to execute the following operations: operations 218A to 218B.

Operation 218A includes rechecking (either directly or indirectly via the auxiliary controller 304), while the room 904 is being sanitized, whether the occupancy-indication signals (received from each sensor assembly 102) indicate that there is someone present in the room 904 (this rechecking is done regardless of whether the sensor assembly 102 is associated with the primary controller 302 or any of the auxiliary controllers 304).

Operation 218B includes confirming (based on the recheck operation 218A), whether the room 904 is occupied or is not occupied while the room 904 is undergoing sanitization (being sanitized).

Once operation 218 is completed, operational control is transferred to any one of: (A) operation 220 (for the case where the primary controller 302 confirms that the room 904 is occupied while the room 904 is being sanitized), and (B) operation 222 (for the case where the primary controller 302 confirms that the room 904 is not occupied while the room 904 is being sanitized).

Operation 220 includes directing the processor 200 of the primary controller 302 to execute the following operations: operations 220A to 220C. Once operation 220 is competed, operational control is transferred to operation 214.

Operation 220A includes deactivating the sanitation-light sources 106 (which are deployed in the room 904, for the case where operation 218 caused the primary controller 302 to determine that the room 904 is occupied while the room 904 is being sanitized). This operation deactivates the sanitation-light sources 106 during sanitization of the room 904 for the case where someone managed to evade detection by the sensor assembly 102 before the sanitation-light sources 106 were activated.

Operation 220B includes deactivating the door-locking mechanism 104 (for the case where operation 218 caused the primary controller 302 to determine that the room 904 was occupied while the room 904 was being sanitized).

Operation 220C includes transmitting the display signal to the display assembly 112 in such a way that the display assembly 112 indicates that the room 904 is available for usage.

Operation 222 includes directing the processor 200 of the primary controller 302 to execute the following operations: operations 222A to 222B. Once operation 222 is completed, operational control is transferred to operation 224.

Operation 222A includes activating each sanitation-light source 106 that is deployed in the room 904; this is done in such a way that the sanitation-light sources 106 emit a sanitization light for sanitizing a predetermined portion of the room 904 for a predetermined sanitization time (for the case where the primary controller 302 determined that the room 904 was unoccupied after the room 904 was locked by the door-locking mechanism 104).

Operation 222B includes deactivating each sanitation-light source 106 that is deployed in the room 904 (for the case where the predetermined sanitization time has lapsed).

Operation 224 includes directing the processor 200 of the primary controller 302 to execute the following operations: operations 224A to 224B. Once operation 224 is completed, operational control is transferred to operation 226.

Operation 224A includes periodically checking each sensor assembly 102 (check either directly or indirectly via the auxiliary controller 304) that is deployed in the room 904 (which may indicate that a person 908 is present in the room 904 while the room 904 is undergoing sanitization). This is done regardless of whether the sensor assembly 102 is associated with the primary controller 302 or any of the auxiliary controllers 304.

Operation 224B includes deactivating (either directly or indirectly via the auxiliary controller 304) the sanitation-light sources 106 (which are deployed in the room 904, and for the case where the primary controller 302 determines that a person 908 is present in the room 904 while the room 904 is undergoing sanitization).

Operation 226 includes directing the processor 200 of the primary controller 302 to execute the following operations: operations 226A to 226B. Once operation 226 is completed, operational control is transferred to operation 214.

Operation 226A includes deactivating the door-locking mechanism 104 in such a way that the door 910 may be opened by anyone in order to access the interior space 902 of the room 904 (for the case where the sanitation-light sources 106 (which are deployed in the room 904, and confirmed to be deactivated), because the room 904 has been sanitized and is now ready for occupation.

Operation 226B includes transmitting the display signal to the display assembly 112 in such a way that the display assembly 112 indicates that the room 904 is available (for usage).

Referring to the embodiment as depicted in FIG. 5, the program 204 is schematically depicted as a flow chart of operations. The operations of the program 204 are described with sufficient details so that a person skilled in the art can form (prepare) the programmed instructions using a high-level computer program, which may then be converted into executable-coded instructions configured to direct the processor 200 (of the auxiliary controller 304) to perform various operations (as described below).

Operation 312 includes directing the processor 200 of the auxiliary controller 304 to operate in an initialization mode (also called a reset mode), in which the auxiliary controller 304 performs operations 312A to 312C. Once operation 312 is completed, operational control is transferred to operation 314.

Operation 312A includes deactivating the sanitation-light source 106 (which is associated with or connected to the auxiliary controller 304), so that the sanitation-light source 106 becomes deactivated and the sanitation light (generated and emitted by the sanitation-light source 106) is not exposed to anyone positioned in the room 904.

Operation 312B includes transmitting, to the primary controller 302 via the network 912, a confirmation signal that the sanitation-light source 106 (which is associated with or connected to the auxiliary controller 304) has been deactivated.

Operation 312C includes (for the case where any of the sanitation-light sources 106 are not operational or are not responsive to the deactivation command) transmitting (via the network 912) an error code to the display assembly 112. The error code is provided by (transmitted by) the primary controller 302 (in an indirect manner, or a direct manner) to the display assembly 112). The error code becomes displayed by the display assembly 112. The error code indicates that the sanitation-light source 106 (of the auxiliary controller 304) is defective and needs immediate replacement, along with a system reset if desired.

Operation 314 includes directing the processor 200 of the auxiliary controller 304 to execute operations 314A to 314C. Once operation 314 is completed, operational control is transferred to operation 316.

Operation 314A includes periodically monitoring and receiving the occupancy-indication signal from the sensor assembly 102 (which is associated with or connected to the auxiliary controller 304).

Operation 314B includes checking or determining whether a portion of the room 904 is occupied based on whether the occupancy-indication signal (which was received from the sensor assembly 102, and which is associated with or connected to the auxiliary controller 304) indicates that there is at least one or more persons 908 present in a portion of the room 904.

Operation 314C includes (for the case where the room 904 is occupied by at least one or more persons 908) continuing to ensure that the sanitation-light source 106 (which is associated with the auxiliary controller 304) remains deactivated.

Operation 316 includes directing the processor 200 of the auxiliary controller 304 to transmit an indication signal (via the network 912) to the primary controller 302 that the sensor assembly 102 (which is associated with the auxiliary controller 304) provides an indication signal (the indication signal indicates a portion of the room 904 is unoccupied by anyone). The door 910 may be locked (by the primary controller 302) so that the room 904 may be sanitized (provided that there is no other conflicting evidence or occupancy signal that may be provided by any other auxiliary controller 304 to the primary controller 302). Once operation 316 is completed, operational control is transferred to operation 318.

Operation 318 includes directing the processor 200 of the auxiliary controller 304 to execute operations 318A to 318B.

Operation 318 A includes rechecking, before the room 904 is to be sanitized, whether the sensor assembly 102 (which is associated with the auxiliary controller 304) indicates that there is someone present in the room 904 and therefore the room 904 is presently occupied.

Operation 318B includes reconfirming, based on the recheck operation 318A, whether the room 904 is occupied or is not occupied while the room 904 is being sanitized.

Once operation 318 is completed, operational control is transferred to (A) operation 320 (for the case where the auxiliary controller 304 confirmed the room 904 was occupied while the room 904 was being sanitized), or (B) operation 322 (for the case where the auxiliary controller 304 confirmed that the room 904 was not occupied while the room 904 was being sanitized).

Operation 320 includes directing the processor 200 of the auxiliary controller 304 to execute operations 320A to 320B. Once operation 320 is completed, operational control is transferred to operation 314.

Operation 320A includes deactivating the sanitation-light source 106 of the auxiliary controller 304 (for the case where the sensor assembly 102 that is associated with the auxiliary controller 304, indicates (via operation 318) that a portion of the room 904 is occupied while the room 904 is locked and being sanitized).

Operation 320B includes transmitting a request to the primary controller 302 (via the network 912) to deactivate the door-locking mechanism 104 (for the case where the sensor assembly 102 (which is associated with or connected to the auxiliary controller 304) indicates that a part of the room 904 is occupied after the room 904 was locked).

Operation 322 includes directing the processor 200 of the auxiliary controller 304 to execute operations 322A to 322B. Once operation 322 is completed, operational control is transferred to operation 324.

Operation 322A includes activating the sanitation-light source 106 (which is associated with or connected to the auxiliary controller 304) in such a way that the sanitation-light source 106 emits the sanitization light for sanitizing a predetermined portion of the room 904 for a predetermined sanitization time (for the case where the primary controller 302 determines that the room 904 is unoccupied after the room 904 has been locked by the door-locking mechanism 104).

Operation 322 B includes deactivating the sanitation-light source 106 (which is associated with or connected to the auxiliary controller 304, for the case where the predetermined sanitization time has lapsed).

Operation 324 includes directing the processor 200 of the auxiliary controller 304 to execute operations 324A to 324C. Once operation 324 is completed, operational control is transferred to operation 326.

Operation 324A includes periodically checking the sensor assembly 102 (which is associated with or connected to the auxiliary controller 304) which may indicate that a person 908 is present in a portion of the room 904 while the room 904 is undergoing sanitization.

Operation 324B includes deactivating the sanitation-light source 106 (which is associated with the auxiliary controller 304, for the case where the auxiliary controller 304 determines that a person 908 is present in a portion of the room 904 while the room 904 is undergoing sanitization).

Operation 324C includes transmitting, via the network 912, a request to deactivate all sanitation-light sources 106 deployed in the room 904 (regardless of whether the sanitation-light sources 106 are connected to the primary controller 302 or any other auxiliary controller 304, for the case where the auxiliary controller 304 determines that a person 908 is present in a portion of the room 904 while the room 904 is undergoing sanitization).

Operation 326 includes directing the processor 200 of the auxiliary controller 304 to transmit (via the network 912) a signal to the primary controller 302 to request the primary controller 302 to deactivate the door-locking mechanism 104 in such a way that the door 910 may be opened by anyone in order to access the interior space 902 of the room 904 (for the case where the sanitation-light source 106 (which is associated with the auxiliary controller 304) is confirmed to be deactivated; for instance, the room 904 has been completely sanitized). Once operation 326 is completed, operational control is transferred to operation 314.

Figure 6:
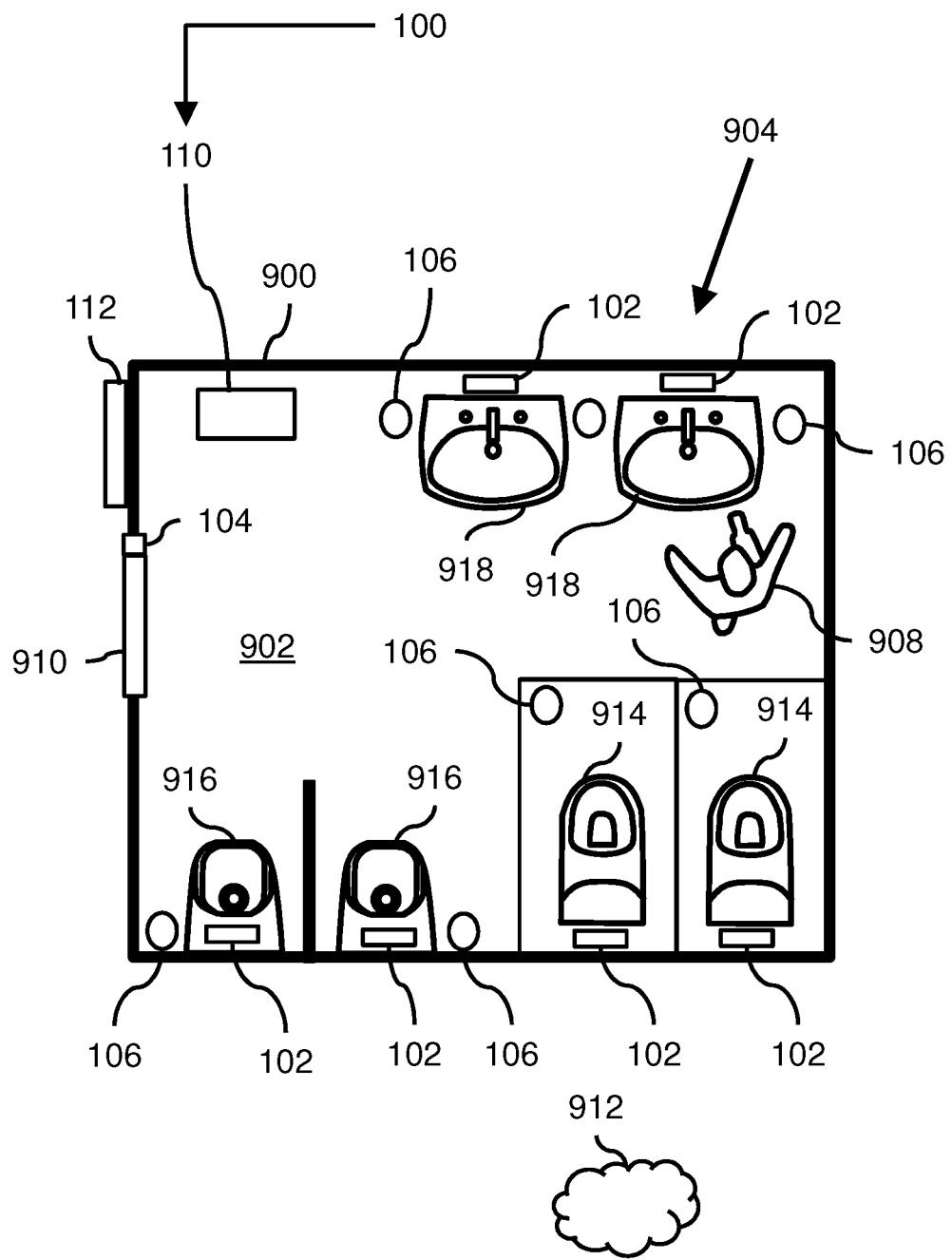
FIG. 6 depicts a top view of the embodiment of the room (as depicted in FIG. 1), in which an embodiment of the sanitization system (as depicted in FIG. 1) is installed in association with the room.

FIG. 6 depicts a top view of the embodiment of the room 904 (of FIG. 1), in which an embodiment of the sanitization system 100 (of FIG. 1) is installed in association with the room 904.

In accordance with the embodiment as depicted in FIG. 6, at least two or more sensor assemblies 102 and at least two or more sanitation-light sources 106 are deployed in the room 904, in which the sensor assemblies 102 and the sanitation-light sources 106 are not attached to any housing that supports the control system 110. Each of the sensor assemblies 102 and the sanitation-light sources 106 are positioned in the room 904, and are either directly connected (via hard wiring) or indirectly connected (via a wireless manner such as the network 912) to the control system 110. The sensor assemblies 102 and the sanitation-light sources 106 each have their own respective housing assembly.

Figure 7:
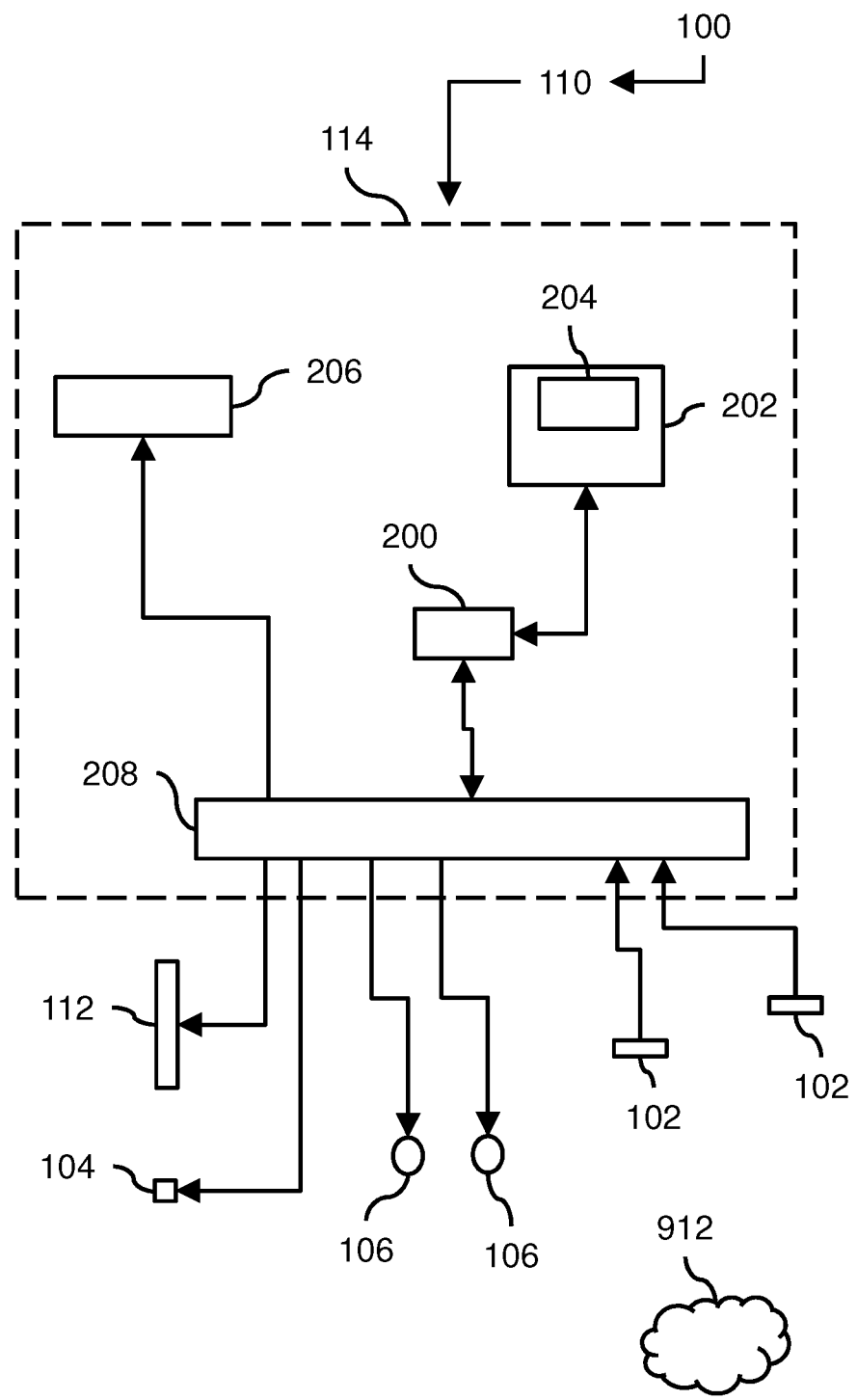
FIG. 7 depicts a schematic view of an embodiment of the sanitization system of FIG. 6.

FIG. 7 depicts a schematic view of an embodiment of the sanitization system 100 of FIG. 6.

Referring to the embodiments as depicted in FIG. 6 and FIG. 7, the housing assembly 114, which houses the control system 110, does not house any sensor assemblies 102 and does not house any sanitation-light sources 106. The control system 110 is configured to cooperate with the sensor assemblies 102 and the sanitation-light sources 106 that may be deployed in the room 904 (as may be required for a particular room layout).

The apparatus includes (and is not limited to) the sanitization system 100. The sanitization system 100 is configured to sanitize, at least in part, the interior space 902 of the room 904. The room 904 may be provided by (A) the stationary structure 906, of which an embodiment is depicted in FIG. 10 or FIG. 11, or (B) the movable structure 907, of which an embodiment is depicted in FIG. 12. The sanitization system 100 includes (and is not limited to) the control system 110 configured to be positioned relative to (such as, positioned in or positioned outside of) the interior space 902 of the room 904. The control system 110 is also configured to be in electrical communication with (operatively coupled to or connected with either a hard wire or via a wireless connection) to: (A) the sensor assembly 102 configured to be positioned in the interior space 902 of the room 904, (B) the door-locking mechanism 104 configured to be operatively connected to the door 910, in which the door 910 is an entrance to the interior space 902 of the room 904, and (C) the sanitation-light source 106 configured to be positionable in the interior space 902 of the room 904.

Figure 8:
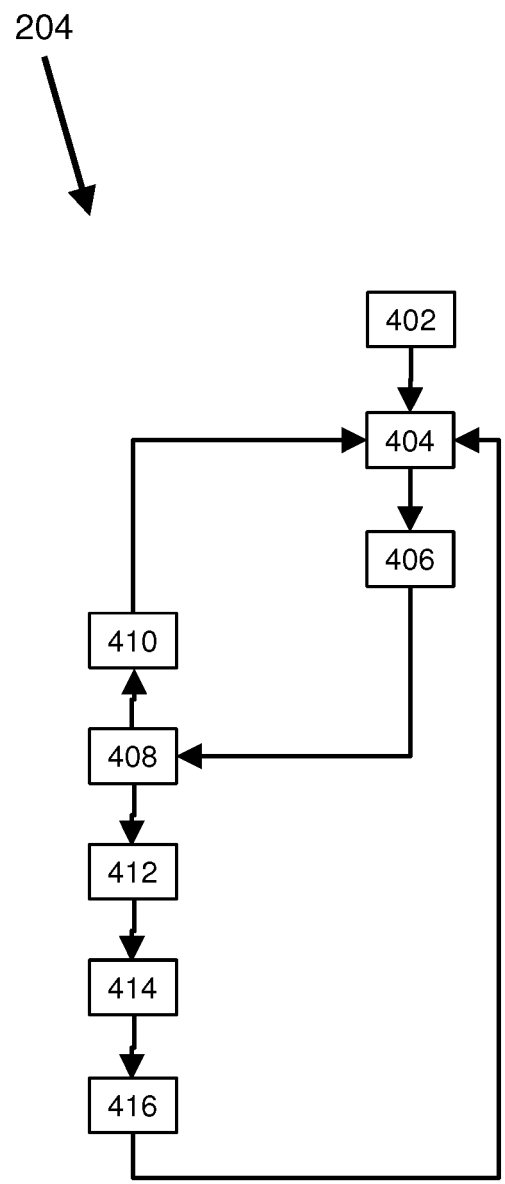
FIG. 8 and FIG. 9 depict a third flow chart (FIG. 8) and a fourth flow chart (FIG. 9) indicating operations of the embodiment of the sanitization system of FIG. 7.
Figure 9:
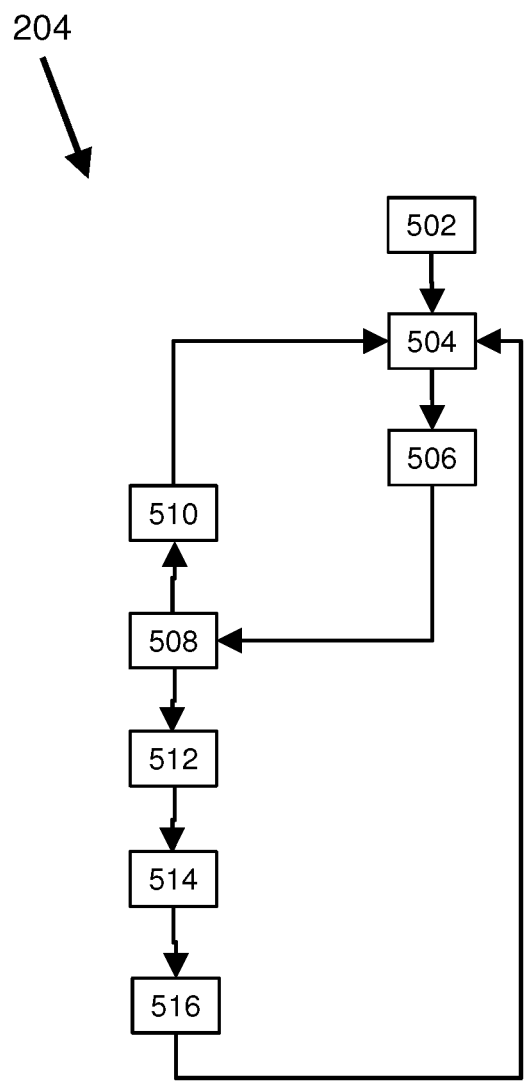

FIG. 8 and FIG. 9 depict a third flow chart (FIG. 8) and a fourth flow chart (FIG. 9) indicating operations of the embodiment of the sanitization system 100 of FIG. 7.

Referring to the embodiment as depicted in FIG. 8, the program 204 is schematically depicted as a flow chart of operations. The operations of the program 204 are described with sufficient details so that a person skilled in the art can form (prepare) the programmed instructions using a high-level computer program, which may then be converted into executable-coded instructions configured to direct the processor 200 (of the control system 110) to perform various operations (as described below).

Operation 402 includes directing the processor 200 of the control system 110 to operate in an initialization mode (also called a reset mode), in which the control system 110 performs or executes operations 402A to 402B. Once operation 402 is completed, operational control is transferred to operation 404.

Operation 402A includes deactivating the sanitation-light source 106 or the sanitation-light sources 106 (which are associated with or connected to the control system 110), so that the light from the sanitation-light source 106 is not exposed to anyone positioned in the room 904.

Operation 402B includes (for the case where any of the sanitation-light sources 106 are not operational or responsive to the deactivation command) transmitting an error code to a lamp (known and not depicted). The lamp may be conveniently mounted to the housing assembly 114, or any equivalent thereof. The error code is displayed, and the error code indicates that at least one of the sanitation-light sources 106 may be defective and needs immediate replacement, along with a system reset if so desired.

Operation 404 includes directing the processor 200 of the control system 110 to execute operations 404A to 404C. Once operation 404 is completed, operational control is transferred to operation 406.

Operation 404A includes periodically monitoring and receiving the occupancy-indication signal that is transmitted from at least one sensor assembly 102 (which is associated with or connected to the control system 110).

Operation 404B includes checking or determining whether the room 904 is occupied based on whether the occupancy-indication signal (which was received from at least one sensor assembly 102) indicates that there is at least one or more persons 908 present in the room 904.

Operation 404C includes (for the case where the room 904 is occupied by at least one or more persons 908) ensuring that all sanitation-light sources 106 remain deactivated.

Operation 406 includes directing the processor 200 of the control system 110 to transmit a door lock signal to the door-locking mechanism 104 so that the door 910 may be locked, and so that the room 904 may be sanitized (because it was determined that the room 904 is not being used). Once operation 406 is completed, operational control is transferred to operation 408.

An option (variation) for operation 406 may include determining whether a predetermined time (also called a time delay) has lapsed since the last time the room 904 was cleaned or sanitized. If the determination indicates that the predetermined time has lapsed since the last time the room 904 was cleaned or sanitized, then operation 406 includes directing the processor 200 of the control system 110 to transmit a door lock signal to the door-locking mechanism 104 so that the door 910 may be locked, and so that the room 904 may be sanitized (because it was determined that the room 904 is not being used). Once operation 406 is completed, operational control is transferred to operation 408.

Operation 408 includes directing the processor 200 of the control system 110 to execute operations 408A to 408B.

Operation 408A includes rechecking, before the room 904 will be sanitized, whether at least one sensor assembly 102 indicates that there is someone present in the room 904 and therefore the room 904 is presently occupied.

Operation 408B includes reconfirming, based on the recheck operation 408A, whether the room 904 is occupied or is not occupied while the room 904 is being sanitized.

Once operation 408 is completed, operational control is transferred to: (A) operation 410 (for the case where the control system 110 confirmed the room 904 was occupied while the room 904 was being sanitized), or (B) operation 412 (for the case where the control system 110 confirmed the room 904 was not occupied while the room 904 was being sanitized).

Operation 410 includes directing the processor 200 of the control system 110 to execute operations 410A to 410B. Once operation 410 is completed, operational control is transferred to operation 404.

Operation 410A includes deactivating the sanitation-light source 106 (for the case where the sensor assembly 102 (which is associated with the control system 110) provided an occupation indication to the control system 110 that the room 904 was occupied while the room 904 was locked and being sanitized).

Operation 410B includes deactivating the door-locking mechanism 104 (for the case where the sensor assembly 102 (which is associated with the control system 110) provided an occupancy indication to the control system 110 (the occupancy indication indicate that a part of the room 904 was occupied after the room 904 was locked).

Operation 412 includes directing the processor 200 of the control system 110 to execute operations 412A to 412B. Once operation 412 is completed, operational control is transferred to operation 414.

Operation 412A includes activating each sanitation-light source 106 in such a way that the sanitation-light sources 106 emit the sanitization light for sanitizing a predetermined portion of the room 904 for a predetermined sanitization time (for the case where the control system 110 determines that the room 904 is unoccupied after the room 904 has been locked by the door-locking mechanism 104).

Operation 412B includes deactivating the sanitation-light source 106 (in which the sanitation-light source 106 is associated with the control system 110, for the case where the predetermined sanitization time has lapsed).

Operation 414 includes directing the processor 200 of the control system 110 to execute operations 414A to 414B. Once operation 414 is completed, operational control is transferred to operation 416.

Operation 414A includes periodically checking the sensor assembly 102 (which is associated with the control system 110) which may indicate that a person 908 is present in the room 904 while the room 904 is undergoing sanitization.

Operation 414B includes deactivating the sanitation-light sources 106 (for the case where the control system 110 determines that a person 908 is present in at least a portion of the room 904 while the room 904 is undergoing sanitization).

Operation 416 includes directing the processor 200 of the control system 110 to deactivate the door-locking mechanism 104 (via the network 912). This is done in such a way that the door 910 may be opened by anyone in order to access the interior space 902 of the room 904 (for the case where the sanitation-light source 106 (which is associated with the control system 110) is confirmed to be deactivated). For instance, the room 904, which has been sanitized, is now ready for occupation. Once operation 416 is completed, operational control is transferred to operation 404.

Referring to the embodiment as depicted in FIG. 9, the program 204 is schematically depicted as a flow chart of operations. The operations of the program 204 are described with sufficient details so that a person skilled in the art can form (prepare) the programmed instructions using a high-level computer program, which may then be converted into executable-coded instructions configured to direct the processor 200 (of the control system 110) to perform various operations (as described below).

Operation 502 includes directing the processor 200 of the control system 110 to operate in an initialization mode (also called a reset mode), in which the control system 110 performs (executes) operations 502A to 502B. Once operation 502 is completed, operational control is transferred to operation 504.

Operation 502A includes deactivating the sanitation-light source 106, so that the light from the sanitation-light source 106 is not exposed to anyone positioned in the room 904.

Operation 502B includes (for the case where any of the sanitation-light sources 106 are not operational or responsive to the deactivation command) transmitting an error code to the display assembly 112 (in which the error code is displayed by the display assembly 112, and the error code indicates that the sanitation-light source 106 is defective and needs immediate replacement, along with a system reset if desired).

Operation 504 includes directing the processor 200 of the control system 110 to execute operations 504A to 504C. Once operation 504 is completed, operational control is transferred to operation 506.

Operation 504A includes periodically monitoring and receiving the occupancy-indication signal that is transmitted from the sensor assembly 102.

Operation 504B includes checking or determining whether the room 904 is occupied based on whether the occupancy-indication signal (which was received from the sensor assembly 102, and in which the sensor assembly 102 is associated with the control system 110) indicates that there is at least one or more persons 908 present in the room 904.

Operation 504C includes (for the case where the room 904 is occupied by at least one or more persons 908) continuing to ensure that the sanitation-light source 106 remains deactivated.

Operation 506 includes directing the processor 200 of the control system 110 to transmit a door lock signal to the door-locking mechanism 104 so that the door 910 may be locked, and so that the room 904 may be sanitized. Once operation 506 is completed, operational control is transferred to operation 508.

An option (variation) for operation 506 may include determining whether a predetermined time (also called a time delay) has lapsed since the last time the room 904 was cleaned or sanitized. If the determination indicates that the predetermined time has lapsed since the last time the room 904 was cleaned or sanitized, then operation 506 includes directing the processor 200 of the control system 110 to transmit a door lock signal to the door-locking mechanism 104 so that the door 910 may be locked, and so that the room 904 may be sanitized. Once operation 506 is completed, operational control is transferred to operation 508.

Operation 508 includes directing the processor 200 of the control system 110 to execute operations 508A to 508B.

Operation 508A includes rechecking, before the room 904 will be sanitized, whether the sensor assembly 102 (which is associated with the control system 110) indicates that there is someone present in the room 904 and therefore the room 904 is presently occupied.

Operation 508B includes reconfirming, based on the recheck operation 508A, whether the room 904 is occupied or is not occupied while the room 904 is being sanitized.

Once operation 508 is completed, operational control is transferred to: (A) operation 510 (for the case where the control system 110 confirmed the room 904 was occupied while the room 904 was being sanitized), or (B) operation 512 (for the case where the control system 110 confirmed the room 904 was not occupied while the room 904 was being sanitized).

Operation 510 includes directing the processor 200 of the control system 110 to execute operations 510A to 510B. Once operation 510 is completed, operational control is transferred to operation 504.

Operation 510A includes deactivating the sanitation-light source 106 (for the case where the sensor assembly 102 provides an indication that the room 904 is occupied while the room 904 is locked and being sanitized).

Operation 510B includes deactivating the door-locking mechanism 104 (for the case where the sensor assembly 102 (which is associated with the control system 110) provided an occupancy signal indicating that a part of the room 904 was occupied after the room 904 was locked).

Operation 512 includes directing the processor 200 of the control system 110 to execute operations 512A to 512B. Once operation 512 is completed, operational control is transferred to operation 514.

Operation 512A includes activating the sanitation-light source 106 (which is associated with the control system 110) in such a way that the sanitation-light source 106 emits the sanitization light for sanitizing a predetermined portion of the room 904 for a predetermined sanitization time (for the case where the control system 110 determines that the room 904 is unoccupied after the room 904 has been locked by the door-locking mechanism 104).

Operation 512B includes deactivating the sanitation-light source 106 (which is associated with the control system 110) (for the case where the predetermined sanitization time has lapsed).

Operation 514 includes directing the processor 200 of the control system 110 to execute operations 514A to 514B. Once operation 514 is completed, operational control is transferred to operation 516.

Operation 514A includes periodically checking the sensor assembly 102 (which may indicate that a person 908 is present in the room 904 while the room 904 is undergoing sanitization).

Operation 514B includes deactivating the sanitation-light source 106 (for the case where the control system 110 determines that a person 908 is present in the room 904 while the room 904 is undergoing sanitization).

Operation 516 includes directing the processor 200 of the control system 110 to deactivate the door-locking mechanism 104 in such a way that the door 910 may be opened by anyone in order to access the interior space 902 of the room 904 (for the case where the sanitation-light source 106 is confirmed to be deactivated; for instance, the room 904 has been sanitized). Once operation 516 is completed, operational control is transferred to operation 504.

FIG. 10, FIG. 11 and FIG. 12 depict a perspective view (FIG. 10) and top views (FIG. 11 and FIG. 12) of embodiments of the room 904 of FIG. 1.

The room 904 may include any type of room, which may require periodic cleaning (sanitization). The room 904 may include a medical office, a dental office, a change room for a gym, a prison room (a prison cell), a classroom of a school (as depicted in FIG. 10), a hospital room or ward (as depicted in FIG. 11), or a washroom of an airplane (as depicted in FIG. 12).

Unless otherwise specified, relational terms used in these specifications should be construed to include certain tolerances that the person skilled in the art would recognize as providing equivalent functionality. By way of example, the term perpendicular is not necessarily limited to 90.0 degrees, but also to any slight variation thereof that the person skilled in the art would recognize as providing equivalent functionality for the purposes described for the relevant member or element. Terms such as "about" and "substantially", in the context of configuration, relate generally to disposition, location, or configuration that is either exact or sufficiently close to the location, disposition, or configuration of the relevant element to preserve operability of the element within the invention which does not materially modify the invention. Similarly, unless specifically or made clear from its context, numerical values should be construed to include certain tolerances that the person skilled in the art would recognize as having negligible importance as it does not materially change the operability of the invention. It will be appreciated that the description and/or drawings identify and describe embodiments of the apparatus (either explicitly or non-explicitly). The apparatus may include any suitable combination and/or permutation of the technical features as identified in the detailed description, as may be required and/or desired to suit a particular technical purpose and/or technical function. It will be appreciated, that where possible and suitable, any one or more of the technical features of the apparatus may be combined with any other one or more of the technical features of the apparatus (in any combination and/or permutation). It will be appreciated that persons skilled in the art would know that technical features of each embodiment may be deployed (where possible) in other embodiments even if not expressly stated as such above. It will be appreciated that persons skilled in the art would know that other options would be possible for the configuration of the components of the apparatus to adjust to manufacturing requirements and still remain within the scope as described in at least one or more of the claims. This written description provides embodiments, including the best mode, and also enables the person skilled in the art to make and use the embodiments. The patentable scope may be defined by the claims. The written description and/or drawings may help to understand the scope of the claims. It is believed that all the crucial aspects of the disclosed subject matter have been provided in this document. It is understood, for this document, that the phrase "includes" is equivalent to the word "comprising." The foregoing has outlined the non-limiting embodiments (examples). The description is made for particular non-limiting embodiments (examples). It is understood that the non-limiting embodiments are merely illustrative as examples.

What is claimed is:

1. An apparatus, comprising:
 a sanitization system configured to sanitize, at least in part, an interior space of a room, the sanitization system, including:
  a control system being configured to be positioned relative to the interior space of the room; and
  the control system also being configured to be in electrical communication with:
   a sensor assembly being configured to be positioned in the interior space of the room; and
   a door-locking mechanism being configured to be operatively connected to a door, in which the door is an entrance to the interior space of the room; and
   a sanitation-light source being configured to be positionable in the interior space of the room; and
  wherein the control system is further configured to:
   transmit a door-control signal to the door-locking mechanism, for the case where the control system receives a presence status indicator signal, from the sensor assembly, in which the presence status indicator signal indicates that the room is occupied by a person positioned in the interior space of the room, and in which the door-control signal, in use, keeps the door in an unlocked state; and monitor and ensure that:
the sanitation-light source remains in an OFF state; and
the door-locking mechanism does not lock the door while the sanitation-light source remains in the OFF state.

2. The apparatus of claim 1, wherein:
the control system is further configured to:
be in electrical communication with a display assembly that is positioned outside of the room in such a way that the display assembly, in use, receives, from the control system, an occupancy-indication signal, in which the occupancy-indication signal indicates an occupation status of the room.

3. The apparatus of claim 1, wherein:
the control system is further configured to:
receive a presence status indicator signal from the sensor assembly once the sensor assembly, in use, detects a presence of the person located in a predefined portion of the interior space of the room; and
transmit a door-control signal to the door-locking mechanism in response to the control system receiving the presence status indicator signal from the sensor assembly; and
transmit a light-source control signal to the sanitation-light source in response to the control system transmitting the door-control signal to the door-locking mechanism.

4. The apparatus of claim 1, wherein:
the control system is further configured:
to receive a presence status indicator signal from the sensor assembly; and
the sensor assembly is configured to:
detect, at least in part, a presence of the person located in a predefined portion of the interior space of the room; and
transmit a presence status indicator signal to the control system in response to the sensor assembly detecting the presence of the person located in the interior space.

5. The apparatus of claim 4, wherein:
the control system is further configured to transmit a door-control signal to the door-locking mechanism, for the case where the control system receives a presence status indicator signal, from the sensor assembly, indicating that the room is not occupied; and
the door-locking mechanism is configured to lock the door in response to receiving the door-control signal from the control system, in which the door-control signal urges the door-locking mechanism to lock the door where the control system receives the presence status indicator signal, from the sensor assembly, indicating that the room is not occupied; and
the control system is further configured to urge the sanitation-light source to emit a sanitization light for sanitizing the predetermined portion of the room for a predetermined sanitization time, for the case where the control system determined that the room was unoccupied after the room was locked by the door-locking mechanism; and
the door-locking mechanism is further configured to unlock the door in response to receiving a door-control signal from the control system after the predetermined sanitization time has lapsed, in which the door-control signal urges the door-locking mechanism to unlock the door and in use the door-locking mechanism, unlocks the door.

6. The apparatus of claim 5, wherein:
the control system is further configured to:
transmit a light-source control signal to the sanitation-light source; and
the sanitation-light source is further configured to:
receive the light-source control signal from the control system, in which the light-source control signal, in use, selectively turns ON and OFF the sanitation-light source; and
selectively emit a sanitation light into the interior space of the room, in response to the sanitation-light source receiving the light-source control signal during use, to sanitize, at least in part, the interior space of the room.

7. The apparatus of claim 1, wherein:
the control system is further configured to:
transmit the door-control signal to a door-locking mechanism, for the case where the control system receives a presence status indicator signal, from the sensor assembly, in which the presence status indicator signal indicates that the room is NOT occupied by anyone that is positioned in a predefined portion of the interior space of the room, and in which the door-control signal, in use, keeps the door in a locked state; and
monitor and ensure that:
the door-locking mechanism, in use, maintains the door in a locked stated for the case where the control system determines that an entirety of the room is empty and unoccupied by anyone; and
the sanitation-light source is turned ON for a predetermined period of time.

8. The apparatus of claim 7, wherein:
the control system is further configured to:
turn OFF the sanitation-light source once the predetermined period of time is lapsed; and
transmit a door-control signal to the door-locking mechanism, once the predetermined period of time is lapsed and once the sanitation-light source is turned OFF, so that the door-control signal, in use, urges the door-locking mechanism to unlock the door.

9. The apparatus of claim 1, wherein:
the control system is further configured to:
control, in use, operation of the sanitation-light source once the control system is electrically connected to the sanitation-light source, and the sanitation-light source receives electrical power.

10. The apparatus of claim 1, wherein:
the control system is further configured to:
receive a presence status indicator signal from the sensor assembly, in which the presence status indicator signal indicates that the sensor assembly did not detect, at least in part, a presence of the person positioned in the interior space of the room; and
transmit a door-control signal to the door-locking mechanism a so that the door-control signal, in use, urges the door-locking mechanism to lock the door for the case where the sensor assembly does not detect, at least in part, the presence of the person positioned in the interior space of the room.

11. The apparatus of claim 1, wherein:
the control system is configured to:
turn ON the sanitation-light source for the case where:
the control system, in use, transmitted a door-control signal to the door-locking mechanism; and
the control system, in use, did not receive a presence status indicator signal from the sensor assembly, that indicates detection of a presence of the person positioned in the interior space of the room.

12. The apparatus of claim 1, wherein:
the control system is further configured to:
  turn OFF the sanitation-light source once a predetermined time duration has lapsed after the control system had turned ON the sanitation-light source.

13. The apparatus of claim 1, wherein:
the control system is further configured to:
  transmit a door-control signal to the door-locking mechanism so that the door-control signal, in use, urges the door-locking mechanism to unlock the door.

14. The apparatus of claim 1, wherein:
the control system is further configured to:
  be housed and supported by a housing assembly, in which the housing assembly is configured to be positionable in the interior space of the room.

15. The apparatus of claim 1, wherein:
the control system includes:
  a first control system and a second control system being locatable at spaced-apart positions in the room; and
  the first control system and the second control system each being configured to be in electrical communication with each other via a network.

16. The apparatus of claim 1, wherein:
the control system is further configured to:
  cooperate with the sensor assembly that is configured to be supported by a housing assembly in such a way that the sensor assembly:
  is positionable in the interior space of the room; and
  faces, in use, the interior space of the room once the housing assembly is positioned in the interior space of the room.

17. The apparatus of claim 1, wherein:
the control system is further configured to:
  cooperate with the sanitation-light source that is configured to be supported by a housing assembly in such a way that the sanitation-light source:
  is spaced apart from the sensor assembly; and
  is positionable in the interior space of the room; and
  faces, in use, the interior space of the room once the housing assembly is positioned in the interior space of the room.

18. The apparatus of claim 1, wherein:
the control system is configured to:
  cooperate with the sensor assembly that is configured to be supported by a housing assembly in such a way that:
  the sensor assembly is positionable in the interior space of the room, and
  the sensor assembly, in use, faces the interior space of the room once the housing assembly is positioned in the interior space of the room; and
  cooperate with the sanitation-light source that is configured to be supported by the housing assembly in such a way that:
  the sanitation-light source is spaced apart from the sensor assembly, and
  the sanitation-light source is positionable in the interior space of the room, and
  the sanitation-light source, in use, faces the interior space of the room once the housing assembly is positioned in the interior space of the room.

19. An apparatus, comprising:
a sanitization system configured to sanitize, at least in part, an interior space of a room, the sanitization system, including:
  a sensor assembly being configured to be positioned in the interior space of the room; and
  a sanitation-light source being configured to be positionable in the interior space of the room; and
  a control system; and
  a housing assembly being configured to house and support the control system, the sensor assembly, and the sanitation-light source; and
  the control system being configured to:
    be positioned relative to the interior space of the room; and
    be in electrical communication with:
      the sensor assembly; and
      the sanitation-light source; and
      a door-locking mechanism being configured to be operatively connected to a door, in which the door is an entrance to the interior space of the room; and
      a display assembly being positioned outside of the room; and
wherein the control system is further configured to:
  transmit a door-control signal to the door-locking mechanism, for the case where the control system receives a presence status indicator signal, from the sensor assembly, in which the presence status indicator signal indicates that the room is occupied by a person positioned in the interior space of the room, and in which the door-control signal, in use, keeps the door in an unlocked state; and
  monitor and ensure that:
    the sanitation-light source remains in an OFF state; and
    the door-locking mechanism does not lock the door while the sanitation-light source remains in the OFF state.

* * * * *